United States Patent [19]
Dedhar

[11] Patent Number: 5,854,202
[45] Date of Patent: Dec. 29, 1998

[54] PEPTIDE FRAGMENTS OF CALRETICULIN, PEPTIDE MIMETICS THEREOF, AND PHARMACEUTICAL COMPOSTIONS COMPRISING SAME

[76] Inventor: Shoukat Dedhar, 59 Drumern Crescent, Richmond Hill, Ontario, Canada, L4C 5H9

[21] Appl. No.: 377,432

[22] Filed: Jan. 24, 1995

[51] Int. Cl.$^6$ .............................. C07K 7/00; A61K 38/04
[52] U.S. Cl. .............................. 514/2; 530/300; 530/324; 530/325; 530/326; 530/327; 530/328; 530/329; 530/330
[58] Field of Search ..................................... 530/350, 300, 530/324, 325, 326, 327, 328, 329, 330; 435/69.1; 514/2

[56] References Cited

U.S. PATENT DOCUMENTS

| | | | |
|---|---|---|---|
| 4,895,719 | 1/1990 | Radhakrishnan et al. | 424/45 |
| 5,217,867 | 6/1993 | Evans et al. | 435/7.1 |
| 5,298,429 | 3/1994 | Evans et al. | 436/501 |
| 5,389,517 | 2/1995 | Wotiz et al. | 435/7.1 |
| 5,426,097 | 6/1995 | Stern et al. | 514/12 |

OTHER PUBLICATIONS

Hsu et al., "Use of Avidin–Biotin–Peroxidase Complex (ABC) in Immunoperoxidase Techniques", *The Journal of Histochemistry and Cytochemistry*, vol. 29, No. 4, pp. 577–580 (1981).
Kozlowski et al., "Advanced Prostatic Carcinoma", *Urologic Clinics of North America*, vol. 18, No. 1, pp. 15–24, (Feb. 1991).
Lee et al., "The Expression and Posttranslational Modification of a Neuron–Specificβ–Tubulin Isotype During Chick Embryogenesis", *Cell Motility and the Cytoskeleton*, vol. 17, pp. 118–132 (1990).
Bert O'Malley, "The Steroid Receptor Superfamily: More Excitement Predicted for the Future", *Molecular Endocrinology*, vol. 4, No. 3, pp. 363–369 (1990).
Opas et al., "Regulation of Expression and Intracellular Distribution of Calreticulin, a Major Calcium Binding Protein of Nonmuscle Cells", *Journal of Cellular Physiology*, vol. 149, pp. 160–171 (1991).
Cao et al., "Cloning of the Promoter for the Avian Integrin $\beta_3$ Subunit Gene and Its Regulation by 1,25–Dihydroxyvitamin $D_3$", *The Journal of Biological Chemistry*, vol. 268, No. 36, Issue of Dec 25, pp. 27371–27380 (1993).
Tai et al., "Association of a 59–Kilodalton Immunophilin with the Glucocorticoid Receptor Complex", *Science*, vol. 256, pp. 1315–1318 (May 29, 1992).
McCauliffe et al., "A Human Ro/SS–A Autoantigen is the Homologue of Calreticulin and is Highly Homologue with Onchocercal RAL–1 Antigen and an Aplysia 'Memory Molecule'", *J. Clin Invest.*, vol. 86, pp. 332–335 (Jul. 1990).
Darbre and King, "Progression to Steroid Insensitivity Can Occur Irrespective of the Presence of Functional Steroid Receptors", *Cell*, vol. 51, pp. 521–528 (Nov. 20, 1987).

Richard J. Stanten, "Clinical Review 37", *Journal of Clinical Endocrinology and Metabolism*, vol. 75, No. 3, pp. 685–689 (1992).
Lebeau et al., "P59, an hsp 90–binding Protein", *The Journal of Biological Chemistry*, vol. 267, No. 7, pp. 4281–4284 (Mar. 5, 1992).
Scardino et al., "Early Detection of Prostate Cancer", *Human Pathology*, vol. 23, No. 3, pp. 211–222 (Mar. 1992).
Tilley et al., "Detection of Discrete Androgen Receptor Epitopes in Prostste Cancer by Immunostaining: Measurement by Color Video Image Analysis", *Cancer Research*, vol. 54, pp. 4096–4102 (Aug. 1, 1994).
Alexander et al., "Characterization of Posttranslational Modifications in Neuron–specific Class III β–tubulin by Mass Spectometry", *Proc. Natl. Acad. Sci. USA*, vol. 88, pp. 4685–4689 (Jun. 1991).
McCauliffe et al., "Molecular Cloning, Expression, and Chromosome 19 Localization of a Human Ro/SS–A Autoantigen", *J. Clin. Invest.*, vol. 85, pp. 1379–1391 (May 1990).
McBurney and Rogers, "Brief Notes Isolation of Male Embryonal Carcinoma Cells and Their Chromosome Replication Patterns", *Developmental Biology*, vol. 89, pp. 503–508 (1982).
Seed and Sheen, "A Simple Phase–extraction Assay for Chloramphenicol Acryltransferase Activity", *Gene* vol. 67, pp. 271–277 (1988).
Boring et al. "Cancer Statistics, 1993", *CA Cancer J Clin*, vol. 43, No. 1, pp. 7–26 (Jan./Feb. 1993).
Darcy et al., "Mammary Organoids for Immature Virgin Rats Undergo Ductal and Alveolar Morphogenesis when Grown within a Reconstituted Basement Membrane", *Experimental Cell Research*, vol. 196, pp. 49–65 (1991).

(List continued on next page.)

*Primary Examiner*—Stephen Walsh
*Assistant Examiner*—Elizabeth C. Kemmerer
*Attorney, Agent, or Firm*—Burns, Doane, Swecker & Mathis, L.L.P.

[57] ABSTRACT

This invention relates to isolated and purified proteins, such as calreticulin and mimetics of calreticulin, for a novel use of modulating hormone responsiveness. These proteins are useful in gene therapy and in manufacturing pharmaceuticals for treating a variety of diseases, including cancer, osteoporosis and chronic inflammatory disease. The proteins include or bind to an amino acid KXFFYR$^1$R [SEQ ID NO.:1], wherein X is G, A or V and wherein X$^1$ is K or R. This sequence is present in the DNA-binding domain, and is critical for the DNA binding activity, of a variety of hormone receptors, including glucocorticoid receptor, minerolcorticoid receptor, androgen receptor, progesterone receptor, estrogen receptor, retinoic acid receptor, thyroid hormone receptor and vitamin D receptor. Proteins which bind to this sequence may inhibit hormone receptor induced gene transcription. Proteins which include this sequence may promote hormone receptor induced gene transcription. The invention includes isolated DNA molecules for these proteins, methods of treating diseases using these proteins, synthetic peptides and their mimetics, and kits containing these proteins, synthetic peptides or their mimetics.

11 Claims, 7 Drawing Sheets

OTHER PUBLICATIONS

Giguére et al., "Molecular Cloning of cDNA Encoding a Second Cellular Retinoic Acid–binding Protein", *Proc. Natl. Acad. Sci. USA*, vol. 87, pp. 6233–6237 (Aug. 1990).

Luisi et al., "Crystallographic Analysis of the Interaction of the Glucocorticoid Receptor with DNA", *Nature*, vol. 352, pp. 497–505 (Aug. 8, 1991).

Härd et al., "Solution Structure of the Glucocorticoid Receptor DNA–Binding Domain", *Science*, vol. 249, pp. 157–160 (Jul. 13, 1990).

Sucov et al., "Characterization of an Autoregulated Response Element in the Mouse Retinoic Acid Receptor Type β Gene", *Proc. Natl. Acad. Sci. USA*, vol. 87, pp. 5392–5396 (Jul. 1990).

Tilley et al., "Androgen Receptor Gene in Human Prostate Carcinoma Cell Lines", *Cancer Research*, vol. 50, pp. 5382–5386 (Sep. 1, 1990).

Quarmby et al., "Expression and Localization of Androgen Receptor in the R–3327 Dunning Rat Prostatic Adenocarcinoma", *Cancer Research*, vol. 50, pp. 735–739 (Feb. 1, 1990).

Baksh and Michalak, "Expression of Calreticulin in *Escherichia coli* and Identification of Its $Ca^{2+}$Binding Domains", *The Journal of Biological Chemistry*, vol. 266, No. 32, pp. 21458–21465 (Nov. 15, 1991).

Fliegel et al., "Molecular Cloning of the High Affinity Calcium–binding Protein (Calreticulin) of Skeletal Muscle Sarcoplasmic Reticulum", *The Journal of Biological Chemistry*, vol. 264, No. 36, pp. 21522–21528 (Dec. 25, 1989).

Donald S. Coffey, "Prostate Cancer an Overview of an Increasing Dilemma", *Cancer Supplement*, vol. 71, No. 3, pp. 880–886 (Feb. 1, 1993).

Peter J. Fuller, "The Steroid Receptor Superfamily: Mechanisms of Diversity", *the FASEB Journal*, vol. 5, pp. 3092–3099 (Dec. 1991).

Dedhar et al. "Inhibition of Nuclear Hormone Receptor Activity by Calreticulin", *Nature*, vol. 367, pp. 480–483 (Feb 3, 1994).

Rojiani et al., "In Vitro Interaction of a Polypeptide Homologous to Human Ro/SS–A Antigen (Calreticulin) with a Highly Conserved Amino Acid Sequence in the Cytoplasmic Domain of Integrin α Subunits", *Biochemistry*, vol. 30, No. 41, pp. 9859–9866 (1991).

Burns et al., "Modulation of Gene Expression by Calreticulin Binding to the Glucocorticoid Receptor", *Nature*, vol. 367, pp. 476–480 (Feb. 3, 1994).

Shoukat Dedhar, "Novel Functions for Calreticulin: Interaction with Integrins and Modulation of Gene Expression", *Trends in Biochemical Sciences*, vol. 19, No. 7, pp. 269–271 (Jul. 1994).

Michalak et al., "Calreticulin", *Biochemistry Journal*, vol. 285, pp. 681–692 (1992).

Dedhar et al., "Specific Alterations in the Expression of α3β1 and α6β4 Integrins in Highly Invasive and Metastatic Variants of Human Prostate Carcinoma Cells Selected by in vitro Invasion Through Reconstituted Basement Membrane", *Clinical & Experimental Metastasis* vol. 11, No. 5, pp. 391–400 (1993).

Leung–Hagesteijn et al., "Cell Attachment to Extracellular Matrix Substrates is Inhibited Upon Downregulation of Expression of Calreticulin, an Intracellular Integrin α–subunit–binding Protein", *Journal of Cell Science*, vol. 107, pp. 589–600 (1994).

Tini et al., "An Everted Repeat Mediates Retinoic Acid Induction of the γF–Crystallin Gene: Evidence of a Direct Role Retinoids in Lens Development", *Genes & Development*, vol. 7, pp. 295–307, (1993).

Pratt et al., "Estrogen and Antiestrogen Modulation of MCF7 Human Breast Cancer Cell Proliferation is Associated with Specific Alterations in Accumilation of Insulin–Like Growth Factor–binding Proteins in Conditioned Media", *Cancer Research*, vol. 53, pp. 5193–5198 (Nov. 1, 1993).

Morrison et al., "Prediction of Bone Density from Vitamin D Receptor Alleles", *Nature*, vol. 367, pp. 284–287 (Jan. 20, 1994).

Burns et al. Mol. Biol. Cell 4 Suppl.:135A, 1993.

Desai et al. J. Biol. Chem. 271:15153–15159, 1991.

Bowie et al. Science 247:1306–1310, 1990.

Ngo et al. The Protein Folding Problem and Tertiary Structure Prediction, Merz et al, eds, Birkhauser, Boston, 1994.

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 2
        ( D ) OTHER INFORMATION: /note= "Amino acid 2 wherein Xaa is either Gly, Ala or Val."

( i x ) FEATURE:
    ( A ) NAME/KEY: Peptide
    ( B ) LOCATION: 5
    ( D ) OTHER INFORMATION: /note= "Amino acid 5 wherein Xaa is
        either Lys or Arg."

( x i ) SEQUENCE DESCRIPTION: SEQ ID NO:1:

Lys  Xaa  Phe  Phe  Xaa  Arg
1                    5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Lys  Gly  Phe  Phe  Arg  Arg
1                    5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Lys  Val  Phe  Phe  Lys  Arg
1                    5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Lys  Ala  Phe  Phe  Lys  Arg
1                    5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Lys  Gly  Phe  Phe  Lys  Arg
1                    5

( 2 ) INFORMATION FOR SEQ ID NO:6:

( i ) SEQUENCE CHARACTERISTICS:

(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

Thr Gly Phe Phe Lys Arg
1               5

(2) INFORMATION FOR SEQ ID NO:7:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

Lys Leu Gly Phe Phe Lys Arg
1               5

(2) INFORMATION FOR SEQ ID NO:8:

(i) SEQUENCE CHARACTERISTICS:
(A) LENGTH: 71 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

Lys Pro Cys Phe Val Cys Gln Asp Lys Ser Ser Cys Tyr His Tyr Cys
1               5                   10                  15

Val Ser Ala Cys Glu Gly Cys Lys Gly Phe Phe Arg Arg Ser Ile Gln
            20                  25                  30

Lys Asn Met Val Tyr Thr Cys His Arg Asp Lys Asn Cys Gln Asp Lys
            35                  40                  45

Ser Ser Cys Tyr His Tyr Cys Val Ser Ala Cys Arg Leu Gln Lys Cys
    50                  55                  60

Phe Glu Val Gly Met Ser Lys
65                  70

(2) INFORMATION FOR SEQ ID NO:9:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

Xaa Gly Phe Phe Lys Arg
1               5

(2) INFORMATION FOR SEQ ID NO:10:

(i) SEQUENCE CHARACTERISTICS:
(A) LENGTH: 7 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:10:

Lys Xaa Gly Phe Phe Xaa Arg
1               5

( 2 ) INFORMATION FOR SEQ ID NO:11:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Lys Ile Gly Phe Phe Lys Arg
1               5

( 2 ) INFORMATION FOR SEQ ID NO:12:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Lys Cys Gly Phe Phe Lys Arg
1               5

( 2 ) INFORMATION FOR SEQ ID NO:13:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Lys Ala Gly Phe Phe Lys Arg
1               5

( 2 ) INFORMATION FOR SEQ ID NO:14:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:14:

Lys Cys Gly Phe Phe Asp Arg
1               5

( 2 ) INFORMATION FOR SEQ ID NO:15:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear (i i) MOLECULE TYPE: peptide (x i) SEQUENCE DESCRIPTION: SEQ ID NO:15:

Arg Met Gly Phe Phe Lys Arg
1               5

(2) INFORMATION FOR SEQ ID NO:16:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:16:

Lys Val Gly Phe Phe Lys Arg
1               5

(2) INFORMATION FOR SEQ ID NO:17:

(i) SEQUENCE CHARACTERISTICS:
(A) LENGTH: 7 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:17:

Lys Cys Gly Phe Phe Asn Arg
1               5

(2) INFORMATION FOR SEQ ID NO:18:

(i) SEQUENCE CHARACTERISTICS:
(A) LENGTH: 15 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:18:

Ala Cys Glu Gly Cys Lys Gly Phe Phe Arg Arg Ser Ile Gln Lys
1               5                   10                  15

(2) INFORMATION FOR SEQ ID NO:19:

(i) SEQUENCE CHARACTERISTICS:
(A) LENGTH: 15 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:19:

Thr Cys Glu Gly Cys Lys Gly Phe Phe Arg Arg Thr Ile Gln Lys
1               5                   10                  15

(2) INFORMATION FOR SEQ ID NO:20:

(i) SEQUENCE CHARACTERISTICS:
(A) LENGTH: 15 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:20:

Thr Cys Glu Gly Cys Lys Gly Phe Phe Arg Arg Ser Met Lys Arg
1               5                   10                  15

( 2 ) INFORMATION FOR SEQ ID NO:21:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Thr Cys Gly Ser Cys Lys Val Phe Phe Lys Arg Ala Val Glu Gly
1               5                   10                  15

( 2 ) INFORMATION FOR SEQ ID NO:22:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Thr Cys Gly Ser Cys Lys Val Phe Phe Lys Arg Ala Ala Ala Gly
1               5                   10                  15

( 2 ) INFORMATION FOR SEQ ID NO:23:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

Thr Cys Gly Ser Cys Lys Val Phe Phe Lys Arg Ala Met Glu Gly
1               5                   10                  15

( 2 ) INFORMATION FOR SEQ ID NO:24:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:24:

Ser Cys Glu Gly Cys Lys Ala Phe Phe Lys Arg Ser Ile Gln Gly
1               5                   10                  15

( 2 ) INFORMATION FOR SEQ ID NO:25:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear (ii) MOLECULE TYPE: peptide (xi) SEQUENCE DESCRIPTION: SEQ ID NO:25:

| Ser | Cys | Glu | Gly | Cys | Lys | Gly | Phe | Phe | Lys | Arg | Thr | Val | Arg | Lys |
|---|---|---|---|---|---|---|---|---|---|---|---|---|---|---|
| 1 |  |  |  | 5 |  |  |  |  | 10 |  |  |  |  | 15 |

(2) INFORMATION FOR SEQ ID NO:26:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

| Thr | Cys | Glu | Gly | Cys | Thr | Gly | Phe | Phe | Lys | Arg | Ser | Ile | Arg | Lys |
|---|---|---|---|---|---|---|---|---|---|---|---|---|---|---|
| 1 |  |  |  | 5 |  |  |  |  | 10 |  |  |  |  | 15 |

(2) INFORMATION FOR SEQ ID NO:27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

| Thr | Cys | Glu | Gly | Cys | Lys | Gly | Phe | Phe | Lys | Arg | Thr | Val | Gln | Lys |
|---|---|---|---|---|---|---|---|---|---|---|---|---|---|---|
| 1 |  |  |  | 5 |  |  |  |  | 10 |  |  |  |  | 15 |

(2) INFORMATION FOR SEQ ID NO:28:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:28:

GTAAAGTACT CCAAGAACCT ATTTGT          26

(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

| Lys | Leu | Arg | Phe | Gly | Phe | Lys |
|---|---|---|---|---|---|---|
| 1 |  |  |  | 5 |  |  |

(2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:30:

Lys Xaa Gly Phe Phe Lys Arg
1               5

( 2 ) INFORMATION FOR SEQ ID NO:31:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Lys Leu Xaa Phe Phe Lys Arg
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

Arg Lys Phe Phe Gly Lys
1               5

( 2 ) INFORMATION FOR SEQ ID NO:33:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Phe Gly Lys Lys Arg Lys
1               5

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Amino acid 1 wherein Lys is
           acetylated."

( x i ) SEQUENCE DESCRIPTION: SEQ ID NO:34:

Lys Gly Phe Phe Lys Arg
1               5

( 2 ) INFORMATION FOR SEQ ID NO:35:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:35:

Lys Gly Leu Phe Lys Arg
1               5

( 2 ) INFORMATION FOR SEQ ID NO:36:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:36:

Lys Gly Phe Leu Lys Arg
1               5

( 2 ) INFORMATION FOR SEQ ID NO:37:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:37:

Lys Gly Tyr Phe Lys Arg
1               5

( 2 ) INFORMATION FOR SEQ ID NO:38:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:38:

Lys Gly Phe Tyr Lys Arg
1               5

( 2 ) INFORMATION FOR SEQ ID NO:39:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:39:

Lys Gly Pro Phe Lys Arg
1               5

( 2 ) INFORMATION FOR SEQ ID NO:40:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:40:

Lys Gly Phe Pro Lys Arg
1               5

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

Lys Phe Gly Phe Lys Arg
1               5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Lys Gly Asp Phe Lys Arg
1               5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

Lys Gly Phe Lys Asp Arg
1               5

( 2 ) INFORMATION FOR SEQ ID NO:44:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:44:

Gly Leu Gly Phe Phe Lys Arg
1               5

( 2 ) INFORMATION FOR SEQ ID NO:45:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:45:

Lys  Leu  Asp  Phe  Phe  Lys  Arg
       1                 5

(2) INFORMATION FOR SEQ ID NO:46:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Lys  Leu  Gly  Arg  Phe  Lys  Arg
       1                 5

(2) INFORMATION FOR SEQ ID NO:47:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:47:

Lys  Leu  Gly  Phe  Arg  Lys  Arg
       1                 5

(2) INFORMATION FOR SEQ ID NO:48:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:48:

Lys  Leu  Gly  Phe  Phe  Gly  Arg
       1                 5

(2) INFORMATION FOR SEQ ID NO:49:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:49:

Lys  Leu  Gly  Phe  Phe  Lys  Gly
       1                 5

PEPTIDE FRAGMENTS OF CALRETICULIN, PEPTIDE MIMETICS THEREOF, AND PHARMACEUTICAL COMPOSTIONS COMPRISING SAME

BACKGROUND OF THE INVENTION

This invention relates to isolated and purified proteins, such as calreticulin and mimetics of calreticulin, for a novel use of modulating hormone responsiveness. These proteins are useful in gene therapy and in manufacturing pharmaceuticals for treating a variety of diseases, including cancer, osteoporosis and chronic inflammatory disease. The proteins include or bind to an amino acid sequence [SEQ ID NO.:1] KXFFX$^1$R, wherein X is either G, A or V and X$^1$ is either K or R. This sequence is present in the DNA-binding domain, and is critical for the DNA binding activity, of a variety of hormone receptors, including glucocorticoid receptor, minerolcorticoid receptor, androgen receptor, progesterone receptor, estrogen receptor, retinoic acid receptor, thyroid hormone receptor and vitamin D receptor. Proteins which bind to this sequence may inhibit hormone receptor induced gene transcription. Proteins which include this sequence may promote hormone receptor induced gene transcription. The invention includes isolated DNA molecules for these proteins, methods of treating diseases using these proteins, synthetic peptides and their mimetics, and kits containing these proteins, synthetic peptides or their mimetics.

The physiology of many organs in mammals is regulated by hormones. These hormones include steroid hormones, thyroid hormones, metabolites of vitamins, such as all trans retinoic acid, 9-cis retinoic acid, vitamin D and its metabolite 1,25 dihydroxyvitamin D3. These hormones are proteins and bind to intracellular receptors which regulate expression of genes (O'Malley, 1990).

There are a variety of receptors which respond to hormones. Osteoblasts and osteoclasts respond to steroid hormones, vitamin D and retinoic acid. Mammary epithelial cells and breast carcinoma cells respond to estrogens, progesterone, retinoic acid and glucocorticoids. Lymphocytes respond to glucocorticoids.

The response of receptors to hormones is particularly important in the development of a number of diseases, including cancer, osteoporosis and chronic inflammatory disease. For example, the vitamin D receptor is strongly implicated in the evolution of osteoporosis (Morrison et al., 1994).

The hormone receptor family is called the nuclear hormone receptor family and consists not only of receptors whose ligands are known, but also of an increasing number of orphan receptors whose ligands are unknown (O'Malley, 1990).

The nuclear hormone receptors can be divided into several domains which include the hormone (ligand) binding domain, the DNA-binding domain and the transactivation domain (O'Malley, 1990). The DNA-binding domain consists of two zinc fingers and is responsible for the receptor's binding to the DNA response elements which are found in the promoter and enhancer regions of the genes whose expression are regulated by these receptors. Once a hormone binds to its receptor, the receptor binds to the DNA thereby inducing gene transcription.

Proteins which modulate hormone receptor induced gene transcription are poorly understood. Such proteins are present in the nucleus of the cell and inhibit or promote the binding of a hormone to its receptor.

To help design pharmaceuticals and therapies for certain diseases, one must understand the function of certain intracellular proteins and their role in modulating hormone responsiveness. Isolation and purification of these proteins would help in assessing whether they inhibit or promote hormone receptor induced gene transcription. Once such proteins are isolated, manipulation of such proteins could further inhibit or promote hormone receptor induced gene transcription. Synthetic peptides which bind to such proteins could be used to promote hormone receptor induced gene transcription. Pharmaceuticals including such peptides or their mimetics could be used to inhibit hormone receptor induced gene transcription. Gene therapy could be used to inhibit or promote hormone receptor induced gene transcription.

A need exists to identify amino acid sequences that are conserved in hormone receptors, so that particular peptides and proteins may be designed and used in modulating hormone responsiveness. This would lead to improved methods of treating a variety of diseases, disorders and abnormal physical states in a mammals by regulating hormone receptor induced gene transcription in mammalian cells.

Calreticulin has been considered to be a resident protein of the endoplasmic reticulum of a cell, where it is thought to behave as a calcium binding protein due to its high capacity calcium binding properties (Michalak et al., 1992). It has been suspected that calreticulin is also present in the nucleus of a cell (Opas et al., 1991), and it has been shown to have a consensus nuclear localization sequence (Michalak, 1992) which is highly homologous to that of histone proteins. However, before this invention, its presence in the nucleus was unconfirmed and its function in the nucleus was unknown.

SUMMARY OF THE INVENTION

This invention relates to an isolated and purified product for use in modulating hormone responsiveness.

In one case, the product for modulating hormone responsiveness is calreticulin which inhibits hormone receptor induced gene transcription. In another case, the product is a mimetic of calreticulin. The product binds to the amino acid sequence [SEQ ID NO.:1] KXFFX$^1$R, wherein X is either G, A or V and wherein X$^1$ is either K or R.

In another case, the product for modulating hormone responsiveness is an antibody to calreticulin or a short peptide. Such an antibody or peptide could promote hormone induced gene transcription by inhibiting calreticulin-hormone receptor interactions. The peptide may be one selected from a group [SEQ ID NOS.:2–6] consisting of: KGFFRR, KVFFKR, KAFFKR, KGFFKR, TGFFKR, or modified derivatives of these peptides.

The invention described in this patent application includes an isolated DNA molecule encoding an amino acid sequence for use in modulating hormone responsiveness. The isolated DNA molecule may encode the amino acid sequence for calreticulin. It may encode the amino acid sequence for part of a mimetic of calreticulin. It may encode a first amino acid sequence that binds to a second amino acid sequence [SEQ ID NO.:1] KXFFX$^1$R, wherein X is either G, A or V and wherein X$^1$ is either K or R.

The invention described in this patent application includes a method of treating a disease, disorder or abnormal physical state in a mammal by regulating hormone receptor induced gene transcription in a cell. The method could include regulating the activity, quantity or stability of a protein for use in hormone receptor induced gene transcription. The protein could be one that includes or binds to the amino acid sequence [SEQ ID NO.:1] KXFFX¹R, wherein X is either G, A or V and wherein X¹ is either K or R. One protein which binds to such sequence is calreticulin. The hormone receptor could be one selected from a group consisting of: glucocorticoid receptor, minerolcorticoid receptor, androgen receptor, progesterone receptor, estrogen receptor, retinoic acid receptor, thyroid hormone receptor, vitamin D receptor and orphan receptors. The disease or disorder could be one selected from a group consisting of breast cancer, prostate cancer, promyelocytic leukemia, solid tumors, chronic inflammatory disease, such as arthritis and osteoporosis.

The method of treating the disease could include administering to the mammal a pharmaceutical comprising the protein, or an organic mimetic and a carrier. A suitable carrier could be a lipid vesicle. As an alternative, the method could include decreasing or eliminating the quantity of calreticulin present in the cell; or decreasing the stability of calreticulin present in a cell.

The invention described in this patent application includes a kit containing a pharmaceutical comprising a protein for use in modulating hormone responsiveness together with a carrier. The protein included within the kit would be one that binds to the amino acid sequence [SEQ ID NO.:1] KXFFX¹R, wherein X is either G, A or V and wherein X¹ is either K or R. Such a protein would include calreticulin or a mimetic of calreticulin.

DEFINITIONS

In this application, the following terms have the following meanings, unless the context requires otherwise:

"A" means adenine

"Binds" means that under given conditions of ionic strength and temperature, a particular product binds to a substrate "EDTA" means ethylenediaminetetraacetic acid "EGF" means Epidermal growth factor "ELISA" means enzyme-linked immunosorbent-assay "F" means phenylalanine "FGF" means Fibroblast growth factor "G" means glysine "HPLC" means high performance liquid chromatography "IGF" means insulin-like growth factor "IL-6" means Interleukin 6

"K" means lysine

"KXFFX¹R" [SEQ ID NO.:13] means an amino acid sequence, wherein X is G, A or V and wherein X¹ is K or R "p60" means a 60 kDA protein, calreticulin "PAGE" means polyacrylamide gel electrophoresis "Peptide" includes amino acids, peptides, polypeptides and proteins "R" means arginine "T" means Threonine "TGF-B" means Transforming growth factor-β

"V" means valine

DETAILED DESCRIPTION OF PREFERRED EMBODIMENTS

Figure 1A:
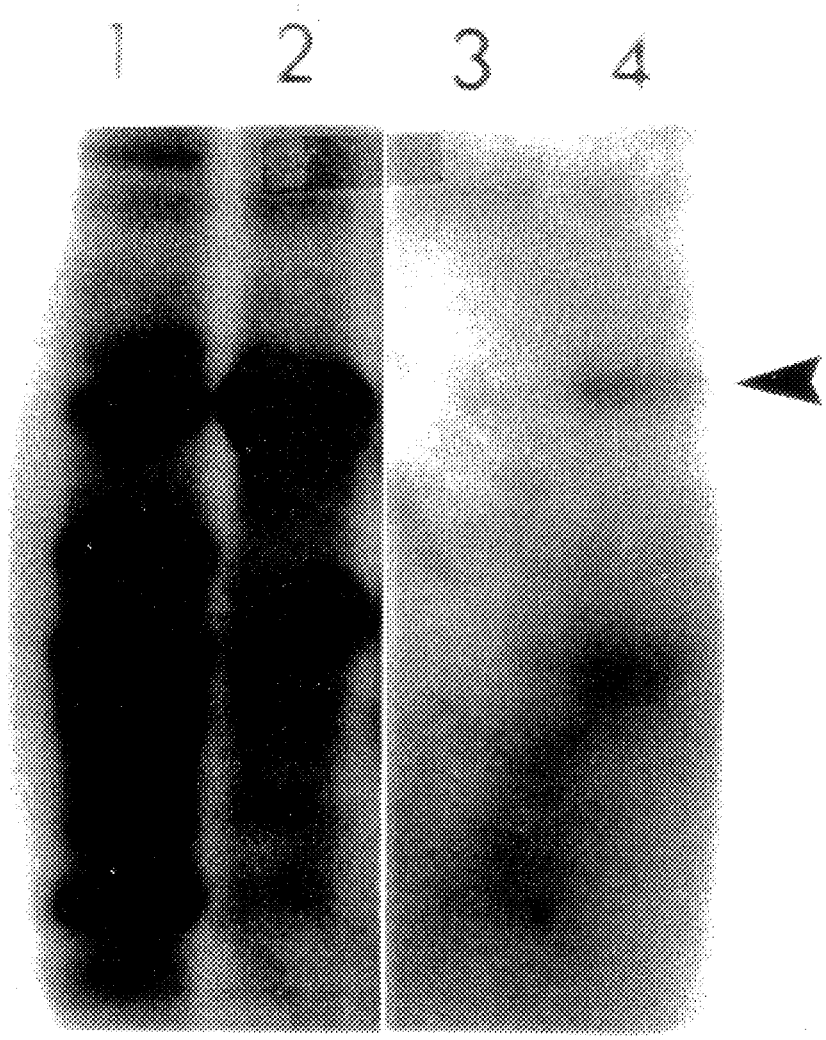
FIG. 1A shows the isolation of p60 (calreticulin) from nuclei by affinity chromatography on [SEQ ID NO.:7] KLGFFKR-sepharose.

A highly homologous amino acid sequence [SEQ ID NO.:1] KXFFX¹R (wherein X is either G, A or V and wherein X¹ is either K or R), has been found to be present in the DNA binding domain of all known members of the steroid hormone receptor family (Fuller, 1991), and amino acids in this sequence make direct contact with nucleotides in their DNA responsive elements, and are crucial for DNA binding (Luisi, 1991).

By way of example, the amino acid sequence [SEQ NOS.:2–5 and 8–9] of the DNA binding domain of RAR is set out below:

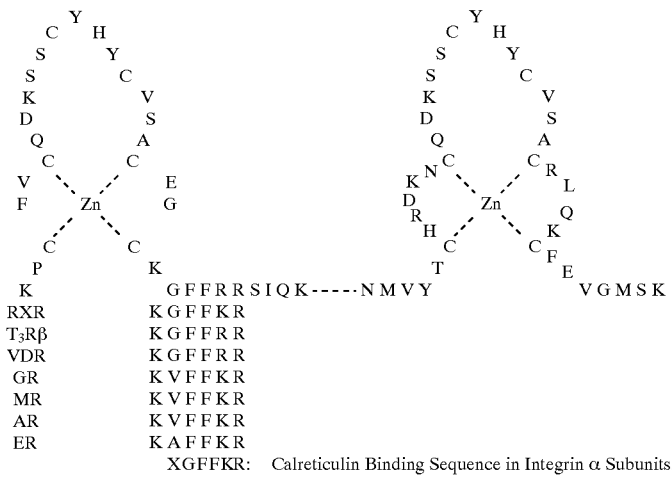

XGFFKR: Calreticulin Binding Sequence in Integrin α Subunits.

Naturally occurring and recombinant calreticulin, inhibit the binding of receptors to DNA. Thus, calreticulin and proteins which mimic calreticulin modulate nuclear hormone receptor regulation of gene transcription.

Calreticulin binds to nuclear hormone receptors by interacting with the amino acid sequence [SEQ ID NO.:1] KXFFX$^1$R. The interaction results in a profound inhibition of nuclear hormone receptor DNA binding activity which can be reversed by soluble competing synthetic peptides with the generic sequence [SEQ ID NO.:1] KXFFX$^1$R. The inhibition of DNA binding by calreticulin can also be reversed by an antibody to calreticulin. Transient or stable overexpression of calreticulin by cDNA transfection also results in the inhibition of nuclear hormone receptor induced gene transcriptional activity. Furthermore, decreased expression of calreticulin by stable transfection of antisense calreticulin cDNA results in increased sensitivity of the cells to hormones due to the increased transcriptional activity of the nuclear hormone receptor.

Hence, a proportion of nuclear hormone receptors may be occupied by calreticulin in a constitutive manner, and decreased regulation of expression of calreticulin may therefore result in an effective increase in the number of unoccupied receptors leading to increased transcriptional activity of these receptors.

By this invention, hormonal sensitivity can be manipulated by (i) increasing or decreasing the intracellular concentration of calreticulin, or (ii) by inhibiting the interaction of calreticulin with nuclear hormone receptors by peptides, peptide mimetics, and antibodies against calreticulin or the KXFFX$^1$R sequence [SEQ ID NO.:1].

The nuclear hormone receptors that interact with calreticulin include androgen receptor, retinoic acid receptors (RAR and RXR), glucocorticoid receptor, and the vitamin D receptor. In all of these cases, calreticulin inhibits receptor binding to DNA, and overexpression of calreticulin results in an inhibition of receptor mediated transcriptional activity. In the case of the retinoic acid receptor system, the decreased regulation of expression of calreticulin results in an increased sensitivity of the cells to differentiation by retinoic acid.

For the following examples: cell lines were obtained from American Type Culture Collection—ATCC; Chemical reagents were purchased from Sigma Chemicals, St. Louis, Mo.; BioRad, Richmond, Calif.; and Amersham Corp., Oakville, ON; Radioisotopes were purchased from Amersham Corp., Oakville, ON; Peptides were synthesized by HSC/Pharmacia Biotechnology Service and Department of Clinical Biochemistry, University of Toronto; Oligonucleotides were synthesized by University of Toronto—Carbohydrate Research Group; Centrifuges used were from Beckman or Eppendorf.

EXAMPLE 1

Calreticulin is Present in Nucleus Cells

The conservation of the KX$^2$GFFX$^3$R [SEQ ID NO.:6] in the α-subunits of integrins is shown in Table I.

A computer search of the Swiss protein data bank for the presence of this sequence motif in other proteins revealed that a highly homologous sequence is present in the DNA binding domain of all members of the nuclear hormone receptors (Table 1) (Fuller, 1991; Carson-Jurica,et al., 1990). Because amino acids in this motif have been demonstrated to be essential for the binding of nuclear hormone receptors to their DNA responsive elements (Luisi et al., 1991; Haird et al., 1990), we wanted to determine whether a 60 kDa protein isolated by affinity chromatography on a KLGFFKR-sepharose affinity matrix [SEQ ID NO.:7] (Rojiani et al., 1991) could modulate DNA binding and transcriptional activities of nuclear hormone receptors.

TABLE 1

Conservation of an Amino Acid Sequence Motif in the Integrin Alpha-subunit Cytoplasmic Domains and in the Steroid Hormone Receptor Family

| | Integrins | | | Steroid Nuclear Receptors | |
|---|---|---|---|---|---|
| a1 | KIGFFKR | [SEQ ID NO.:11] | RARa | ACEGCKGFFRRSIQK | [SEQ ID NO.:18] |
| a2 | KLGFFKR | [SEQ ID NO.:7] | T₃Rb | TCEGCKGFFRRTIQK | [SEQ ID NO.:19] |
| a3 | KGGFFKR | [SEQ ID NO.:12] | VDR | TCEGCKGFFRRSMKR | [SEQ ID NO.:20] |
| a4 | KAGFFKR | [SEQ ID NO.:13] | GR | TCGSCKVFFKRAVEG | [SEQ ID NO.:21] |
| a5 | KLGFFKR | [SEQ ID NO.:7] | MR | TCGSCKVFFKRAVEG | [SEQ ID NO.:21] |
| a6(A) | KCGFFKR | [SEQ ID NO.:12] | AR | TCGSCKVFFKRAAAG | [SEQ ID NO.:22] |
| a6(B) | KCGFFKR | [SEQ ID NO.:12] | PR | TCGSCKVFFKRAMEG | [SEQ ID NO.:23] |
| a7 | KLGFFKR | [SEQ ID NO.:7] | ER | SCEGCKAFFKRSIQG | [SEQ ID NO.:24] |
| a8 (chick) | KCGFFDR | [SEQ ID NO.:14] | RXR | SCEGCKGFFKRTVRK | [SEQ ID NO.:25] |
| av | RMGFFKR | [SEQ ID NO.:15] | Steriod Receptor TR2 | TCEGCTGFFKRSIRK | [SEQ ID NO.:26] |
| Mac-1 | KLGFFKR | [SEQ ID NO.:7] | Nerve growth factor induced protein 1-B | TCEGCKGFFKRTVQK | [SEQ ID NO.:27] |
| p150 | KVGFFKR | [SEQ ID NO.:16] | Early response protein NAK1 | TCEGCKGFFKRTVQK | [SEQ ID NO.:27] |
| PS2 (Drosophila) | KCGFFNR | [SEQ ID NO.:17] | Chorion Factor 1 | SCEGCKGFFKRTVRK | [SEQ ID NO.:25] |

In Table I, the sequences indicated with an asterisk were obtained as described in Rojiani et al, 1991. GR: Glucorticoid receptor; MR: Minerolcorticoid receptor; AR: Androgen receptor; PR: Progesterone receptor; ER: Estrogen receptor.

Although calreticulin contains a KDEL motif at its C-terminus and is therefore thought to be resident in the endoplasmic reticulum (McCauliffe et al., 1990; Fliegel et al., 1989; Michalak et al., 1992), it also has a nuclear targeting signal (McCauliffe et al., 1990; Michalak et al., 1992; Marzluff et al., 1985), raising the possibility that this protein is also present in the nucleus (Michalak et al., 1992). The presence of p60 in nuclei was demonstrated by affinity chromatography of human osteosarcoma cell (HOS) nuclear extracts on [SEQ ID NO.:7] a KLGFFKR-affinity column (FIG. 1).

Nuclei were purified from HOS cells by established methods (Luisi et al., 1991). The purified nuclei were either lysed in PBS containing 1% Triton X-100, 0.1% SDS, 0.5% sodium deoxycholate and 1 mM PMSF, or were applied to a glass coverslip and stained for nuclear antigen with anti-nuclear monoclonal antibody MAB1218 obtained from Chemicon Int. Inc., Tamecula, Calif. The nuclei were visualized by indirect immunofluoresence. The total cellular or nuclear extracts were subjected to affinity chromatography on [SEQ ID NO.:7] a KLGFFKR-affinity matrix, and the p60 isolated (Rojiani et al., 1991).

Cell extracts were prepared from whole cells or from purified nuclei and applied to [SEQ ID NO.:7] KLGFFKR-sepharose affinity matrix. Bound proteins were eluted with EDTA and analyzed by SDS-polyacrylamide gel electrophoresis (Rojiani et al., 1991). The separated proteins were electrophoretically transferred to nitrocellulose filters and probed with an anti-calreticulin antibody. In FIG. 1, Lane 1: Total cellular extract; Lane 2: EDTA eluted material from affinity column to which total cellular extract was applied; Lane 3: Nuclear extract; Lane 4: EDTA eluted material from affinity column to which nuclear extract was applied. Arrow indicates the position of p60.

Figure 1B:
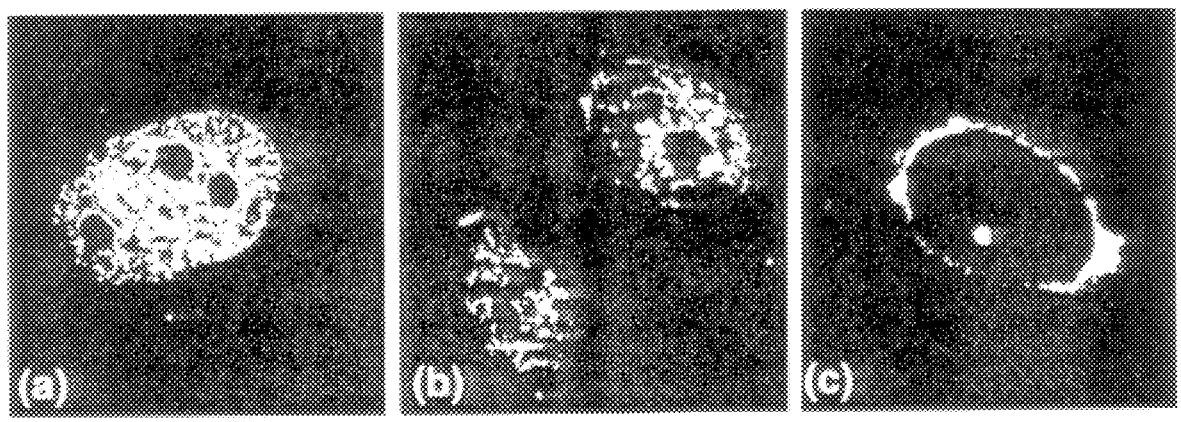
FIG. 1B panels (a)–(c) show immunofluorescent confocal images of TE-85 human osteosarcoma cell nuclei stained with an antibody against calreticulin.

Indirect immunofluoresence of HOS cells or purified nuclei with anti-calreticulin antibody also demonstrated intranuclear calreticulin expression, as shown in FIG. 1B. Confocal microscopy was carried out using a BioRad MRC 500 system. Note the non-nucleolar, intranuclear staining of the cell in (a) and (b), and the complete exclusion of intranuclear staining in the cell in (c). These data suggest that the expression of calreticulin in the nucleus is a regulated process.

These results confirmed the presence of a calreticulin-related p60 protein in nuclei.

EXAMPLE 2

The Sequence KXFFX¹R [SEQ ID NO.:1 ] is Present in All Known Members of the Nuclear Receptor Family As shown in Table I, the sequence [SEQ ID NO.:1] KXFFX¹R is present in all known members of the nuclear receptor family. The region containing this sequence in the DNA-binding domains of these receptors has been shown to play a crucial role in DNA sequence recognition (Luisi et al., 1991). Thus calreticulin, by binding to this common sequence, modulates the binding of all members of the receptor family to DNA. By way of example, we have demonstrated the inhibition by calreticulin of the interaction of the androgen receptor with its DNA response element (see Examples 3 and 4) and of the retinoic acid receptor heterodimer complex (RAR/RXR) with its DNA response element (see Example 5).

EXAMPLE 3

Ability of Calreticulin to Modulate Binding of Nuclear Hormone Receptors In Vitro To determine whether p60 (calreticulin) could directly modulate the binding of nuclear hormone receptors to DNA via the KXFFX¹R sequence [SEQ ID NO.:1], the interaction of the DNA binding domain of recombinant androgen receptor with its hormone responsive element was analyzed by carrying out gel mobility shift assays.

As described in Rennie et al., 1993, DNA binding domain of recombinant rat androgen receptor was prepared as a GST-fusion protein using the pGEX-3X vector and purified by glutathione-agarose affinity chromatography. p60 (calreticulin) was purified by affinity chromatography on [SEQ ID NO.:7] KLGFFKR-sepharose, followed by gel electrophoresis as described in detail in Rojiani et al., 1991. Purified AR and p60 (calreticulin) were found to be greater than 90% and 95% pure, respectively, as determined by SDS-PAGE and Coomassie Blue staining. Recombinant calreticulin (GST-fusion protein) was prepared as described by Baksh and Michalak, 1991. Gel retardation assays were carried out as described by Rennie et al., 1993. To analyze the effect of p60, or recombinant calreticulin, on receptor-DNA binding activity, the AR was pre-incubated with p60 for 30 min at 4° C. To analyze the effects of synthetic peptides, anti-calreticulin antibody, and non-immune IgG on p60 inhibition of AR-ARE binding, the peptide, antibody or IgG were pre-incubated with p60 for 30 min at 4° C. The androgen receptor preparation was then added to these mixtures and further incubated for 30 min at 4° C.

Affinity purified DNA binding domain of the recombinant rat androgen receptor (AR) was pre-incubated with or without the indicated concentrations of purified p60 at 4° C. for 30 min. After this pre-incubation the reaction mixtures were incubated with $^{32}$P-labeled 26 base pair ARE (Rennie et al., 1993) (androgen response element), and analyzed by gel retardation assay. The sequence [SEQ ID NO.:28] of the ARE used was:

5' GTAAAGTACTCCAAGAACCTATTTgt 3'

3' CATTTCATGAGGTTCTTGGATAAAca 5'

Figure 2A:
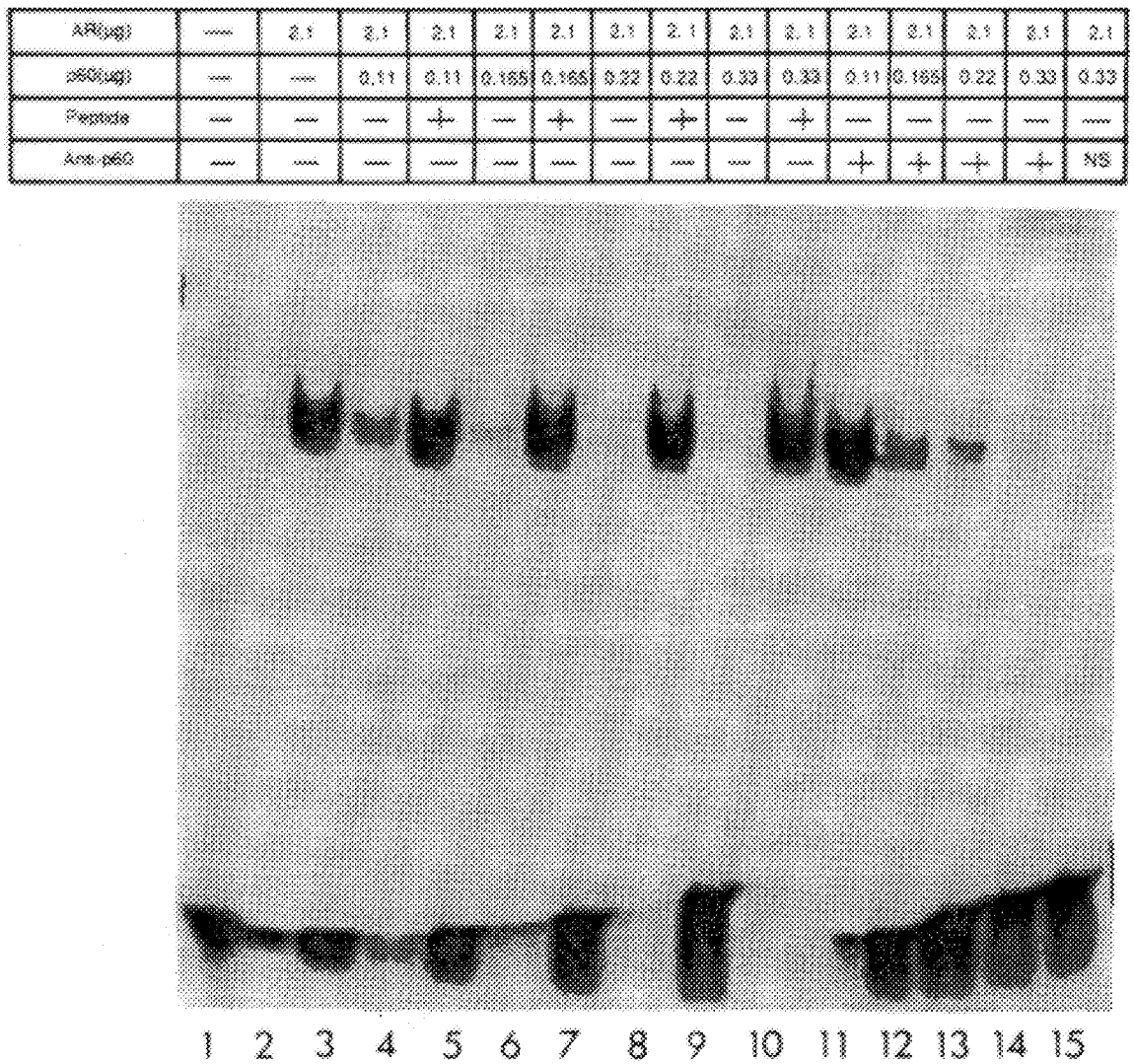
FIG. 2A shows that preincubation of purified p60 (calreticulin) with the recombinant receptor resulted in a dose-dependent inhibition in the formation of the complex between the receptor and the DNA.

In FIG. 2A, the following lanes show the following results: Lane 1 $^{32}$P-labeled ARE by itself; Lane 2: Retardation of ARE by AR; Lane 3: Effect of preincubation of 0.11 mg of purified p60 with AR on AR-ARE binding; Lane 4: Effect of the addition of a 25-fold molar excess of KLG-FFKR synthetic peptide to p60 on AR-ARE binding. Lanes 3, 5, 7, & 9: Effect of increasing concentrations of p60 (from 0.11 mg to 0.33 mg) on AR-ARE binding; Lanes 4, 6, 8, & 10: Reversal of p60 inhibition of AR-ARE binding by KLGFFKR peptide [SEQ ID NO.:7]. Lane 11: Effect of addition of anti-calreticulin antibody to p60 inhibition of AR-ARE binding. Lanes 12–15: Increasing amounts of p60 in the presence of anti-calreticulin antibody. Increasing the p60 concentration overcomes the effect of antibody on p60 inhibition of AR-ARE.

Figure 2B:
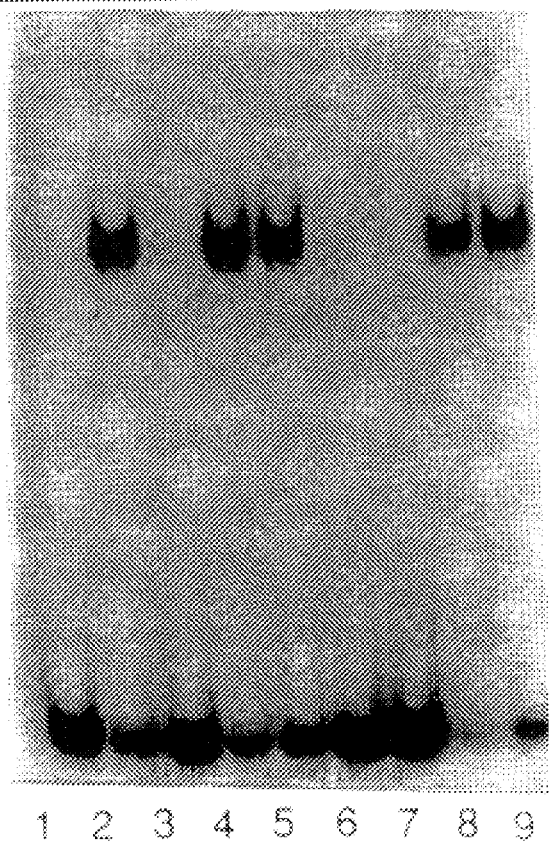
FIG. 2B shows that recombinant calreticulin inhibits the binding of the androgen-receptor to its response element.

In FIG. 2B, the following lanes show the following results: Lane 1: $^{32}$P-labelled ARE alone; Lane 2: Retardation of ARE by AR in the presence of gluthathione-S-transferase (GST); Lane 3: Inhibition by GST-calreticulin (GST-calreticulin) of AR-ARE interaction; Lanes 4 and 5: Reversal of this inhibition by KLGFFKR peptide [SEQ ID NO.:7]; Lanes 6 and 7: Inability of the scrambled peptide [SEQ ID NO.:29] (KLRFGFK) in reversing the effect of calreticulin on AR-ARE interaction; Lanes 8 and 9: The peptide [SEQ ID NO.:3] KVFFKR can also reverse the inhibition by calreticulin of the AR-ARE interaction. The concentration of calreticulin used was 2 mg and the peptides were used at a 50-fold molar excess concentration.

As shown in FIG. 2, the migration of a $^{32}$P-labeled 26 base pair DNA androgen responsive element residing at positions −115 to −140 of the rat probasin gene promoter (Rennie et al., 1993) was retarded by the androgen receptor DNA-binding domain; indicating the formation of a complex between the receptor and the DNA (Rennie et al, 1993). Pre-incubation of purified p60 (calreticulin) with the recombinant receptor resulted in a dose-dependent inhibition in the formation of this complex (FIG. 2A, lanes 3, 5, 7, & 9). The sequence specificity of this inhibition was demonstrated by the finding that the inhibition by p60 (calreticulin) of receptor-DNA binding was reversed by the addition of competing KLGFFKR peptide [SEQ ID NO.:7] (FIG. 2A, lanes 4, 6, 8, & 10) or KVFFKR [SEQ ID NO.:3] (FIG. 2B, lanes 8 and 9), whereas a scrambled peptide [SEQ ID NO.:29] (KLRFGFK) was much less effective (FIG. 2B, lanes 6 and 7). An antibody to calreticulin, which cross-reacts with p60, also reversed this inhibition by p60 (FIG. 2A, lane 11), demonstrating p60 specificity. Non-immune IgG did not have any effect on the inhibition of receptor-DNA interaction by p60 (FIG. 2A, lane 15). Furthermore, neither KLGFFKR peptide, [SEQ ID NO.:7], anti-calreticulin antibody, nor non-immune IgG by themselves had any effect on the receptor-DNA interaction (data not shown). p60 did not effect the binding of AP-1 to DNA, and other proteins of similar size (e.g. bovine serum albumin) also did not have any effect on the nuclear receptor-DNA interaction (data not shown).

Recombinant calreticulin (obtained from Dr. Michalak, Edmonton, Alta) (Baksh et al., 1991), in the form of a GST-fusion protein, also inhibited the binding of the androgen-receptor to its response element (FIG. 2B, lane 2), and this inhibition was also reversed by KVFFKR peptide [SEQ ID NO.:3], (FIG. 2B, lane 2), but not by a scrambled peptide [SEQ ID NO.:29] KLRFGFK (FIG. 2B, lane 1) confirming that the p60 purified on the KLGFFKR affinity matrix [SEQ ID NO.:7] and calreticulin are functionally similar in terms of binding to nuclear hormone receptors, and that a synthetic peptide[SEQ ID NO.:3], KVFFKR can competitively inhibit the binding of calreticulin to the KVFFKR sequence [SEQ ID NO.:3] of the androgen receptor.

EXAMPLE 4

Inhibition of Transcriptional Activity of the Androgen Receptor In Vivo.

To determine whether calreticulin also inhibited the transcriptional activity of the androgen receptor in vivo, expression vectors containing full-length calreticulin (McCauliffe et al., 1990) and androgen receptor (Rennie et al., 1993), cDNAs were co-transfected into Vero fibroblasts together with a chloramphenicol acetyl transferase (CAT) reporter plasmid driven by the mouse mammary tumor virus (MMTV) long terminal repeat (LTR). MMTV-LTR contains androgen response elements (Rennie et al., 1993).

Figure 2C:
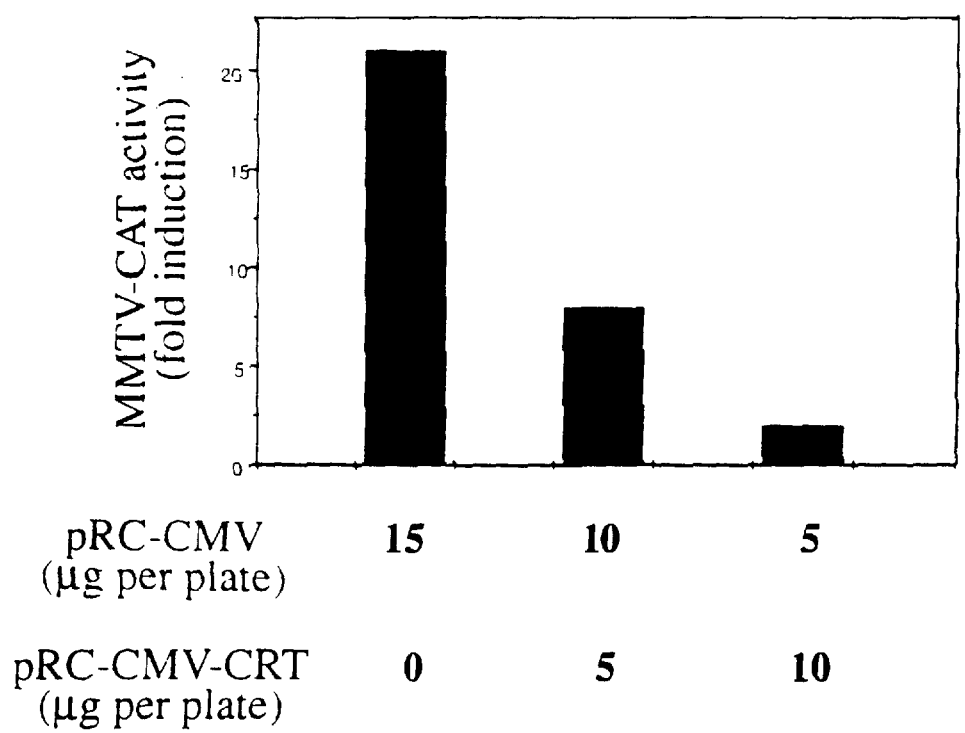
FIG. 2C shows that co-transfection of the calreticulin-containing plasmid resulted in a dose-dependent inhibition of chloramphenicol acetyltransferase activity induced by the androgen receptor.

FIG. 2C shows inhibition of androgen-induced CAT activity by calreticulin. Vero fibroblasts were cotransfected with an MMTV-CAT reporter vector and various amounts of a calreticulin expression vector and the pRC-CMV vector alone (Invitrogen) using the calcium phosphate method (Filmus et al., 1992). In all transfections 10 mg of a β-galactosidase expression vector and 10 mg of an androgen receptor expression vector (Seed et al., 1988) were included. Transfected cells were incubated in medium alone or in the presence of 100 nM R1881 (synthetic androgen) for 12 h. Cells were then lysed and CAT activity measured (Seed et al., 1988). An aliquot of the cell extracts was also assayed for β-galactosidase activity. This activity was used to standardize the measurement of CAT levels in each experiment by taking into account the efficiency of the transfection. Every sample was tested in quadruplicate and the average activity calculated. CAT activity induction as defined as the ratio between the standardized CAT activity of the R1881 treated cells and the corresponding untreated cultures. The Vero cells were grown in a-minimum essential medium containing 10% charcoal-treated calf serum.

As shown in FIG. 2C, co-transfection of the calreticulin containing plasmid resulted in a dose dependent inhibition of CAT activity induced by the androgen receptor. Furthermore, immunoprecipitation of calreticulin from $^{35}$S-methionine/cysteine labeled, androgen receptor transfected Vero cells, resulted in the co-precipitation of the 110 kDa androgen receptor, indicating a direct interaction between calreticulin and the androgen receptor (S. Dedhar and C. Leung-Hagesteijn, unpublished observations).

These data demonstrate that not only can calreticulin bind to the androgen receptor DNA binding domain and inhibit its interaction with the androgen response elements in vitro, it can also inhibit the transcriptional activity of the androgen receptor in vivo. Although other 59 kDa proteins have been found in complexes with several steroid hormone receptors (Lebeau et al., 1992; Tai et al., 1992), they are distinct from calreticulin, and none of them have an effect on binding of the receptors to their DNA responsive elements.

EXAMPLE 5

Regulation by Calreticulin of Hormone Receptor Induced Gene Transcription

In order to demonstrate a physiological significance of the finding that calreticulin can bind to the DNA binding domain of nuclear hormone receptors and modulate their transcriptional activity, we utilized a retinoic acid responsive system i.e. the induction of neuronal differentiation by retinoic acid in P19 embryonal carcinoma cells (McBurney et al., 1982). We predicted that increased expression of calreticulin would suppress retinoic acid induced neuronal differentiation, whereas decreased expression would result in the release of calreticulin inhibition, and allow for a more rapid rate of neuronal differentiation.

The full length 1.9 Kb calreticulin cDNA (McCauliffe et al., 1990) was obtained from Dr. R. D. Sontheimer, Texas and was subcloned into pRC/CMV (Invitrogen, San Diego, Calif.) expression vector in the sense and antisense orientation. pRC/CMV, pRC/CMV-Cal-1 (sense), or pRC/CMV-Cal-2 (antisense) expression plasmids were then transfected into P19 embryonal carcinoma cells by electroporation. Neomycin-resistant transfectant cells were then selected by growth in the presence of 600 mg/ml G418 and the resistant cells were maintained in 100 mg/ml G-418. Cal-1 and Cal-2 transfectants were subcloned by limiting dilution, and the subclones were screened for calreticulin expression by Western blot analysis of cell lysates with an anti-calreticulin antibody (Rojiani et al., 1991).

Retinoic acid neuronal differentiation was induced as described previously (McBurney et al., 1982; Dedhar et al., 1991) and class III β-tubulin expression was analyzed by Western blotting with a class III β-tubulin monoclonal antibody (TuJ1). This antibody was obtained from Dr. A. Frankfurter, University of Virginia, Charlottesville, Va., U.S.A. The bRARE-luciferase transient transfections in p19 (Neo), Cal-1 and Cal-2 cells were carried out as described in Tini et al., 1993. The vector bRARE(3) tk-LUC was constructed by linking 3 copies of the 32 base pair sequence that defines the RARE upstream from the RAR-b gene (de The, et al., 1990; Sucov et al., 1990) to the minimal thymidine kinase promoter and the firefly luciferase gene.

The level of calreticulin expression was estimated by Western blot analysis of cellular lysates (Rojiani et al., 1991) followed by densitometric scanning. For Northern blot analysis total cellular RNA (15 mg) from the indicated cell lines was hybridized to $^{32}$-P-labeled CRABP(II) cDNA (Giguere et al., 1990) at 65° C. using Rapid Hyb buffer (Amersham Corp.). The blot was stripped and reprobed with a mouse actin cDNA probe to check for equal loading of RNA. Values for relative mRNA levels were derived from quantitation of the signal in each lane using a Molecular Dynamics Phosphorimager. CRABPII mRNA levels were normalized against the corresponding actin mRNA signal.

The level of expression of calreticulin was modulated in P19 EC cells by transfection with calreticulin cDNA inserted in the sense or antisense orientation in the pRC/CMV (Invitrogen Corp., San Diego, Calif.) expression vector. P19 EC cell subclones overexpressing calreticulin (Cal-1), or anti-sense transfectants with reduced calreticulin expression (Cal-2), as well as control transfected cells (Neo), were subjected to induction of neuronal differentiation by retinoic acid as described previously (McBurney et al., 1982; Dedhar et al., 1991). The expression of neuron-specific class III β-tubulin (Lee et al., 1990; Alexander et al., 1991) was then analyzed 48 hr (A) or 72 hr (B) after the addition of all-trans retinoic acid (5 mM). Cal-1 (1A2 and 1D2) clones were transfected with pRC/CMV containing calreticulin cDNA in the sense orientation. Cal-2 (1A4 and 1B4) clones were transfected with pRC/CMV containing calreticulin cDNA in the anti-sense orientation. (C): Effect of levels of calreticulin expression on retinoic acid mediated neuronal differentiation.

Cells were stained with anti-class III β tubulin antibody (TuJi) followed by FITC conjugated secondary antibody as described above. A and B: P19 (neo) EC cells; C and D: P19-Cal-1 EC cells; E and F: P19 Cal-2 EC cells. A, C and E; untreated cells. B, D and F: 6 days at RA (0.5 μM) treated cells. The cells were visualized using a Zeiss Axioscop microscope under oil immersion and photographed with Kodak T-Max 400 film. Magnification 100×.

Figures 3A, 3B:
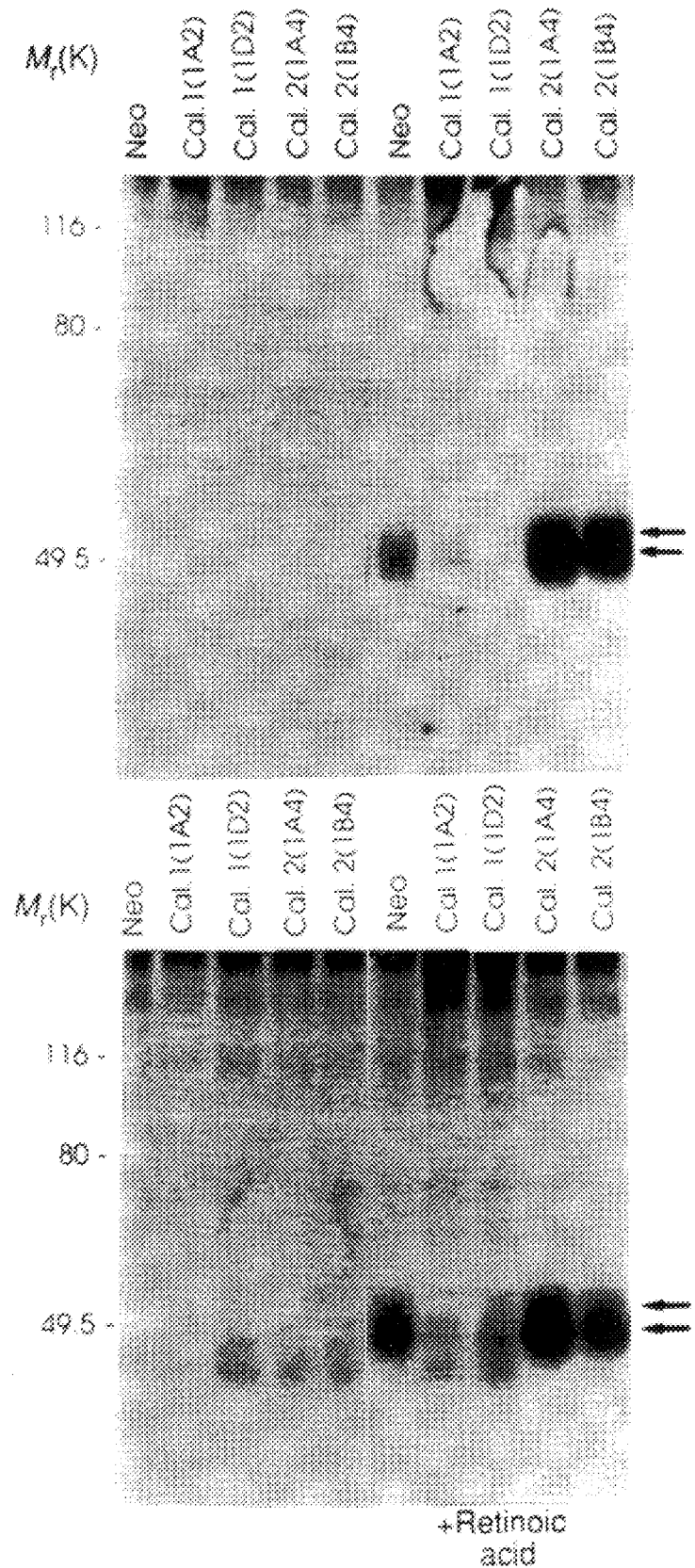
FIG. 3A shows that overexpression of calreticulin by calreticulin cDNA transfection in p19EC cells dramatically suppressed neuronal differentiation, as judged by the expression of a specific early marker of neuronal differentiation class III β-tubulin.
FIG. 3B shows that overexpression of calreticulin by calreticulin cDNA transfection in p19EC cells dramatically suppressed neuronal differentiation, as judged by the expression of a specific early marker of neuronal differentiation class III β-tubulin.

As shown in FIG. 3A and B, overexpression of calreticulin (Cal-1), by calreticulin cDNA transfection in P19 EC cells indeed dramatically suppressed neuronal differentiation, as judged by the expression of a specific early marker of neuronal differentiation, class III β-tubulin (Lee et al., 1990; Alexander et al., 1991). In contrast, decreased expression of calreticulin (Cal-2), by anti-sense calreticulin cDNA transfection, resulted in markedly enhanced expression of class III β-tubulin.

Figure 3C:
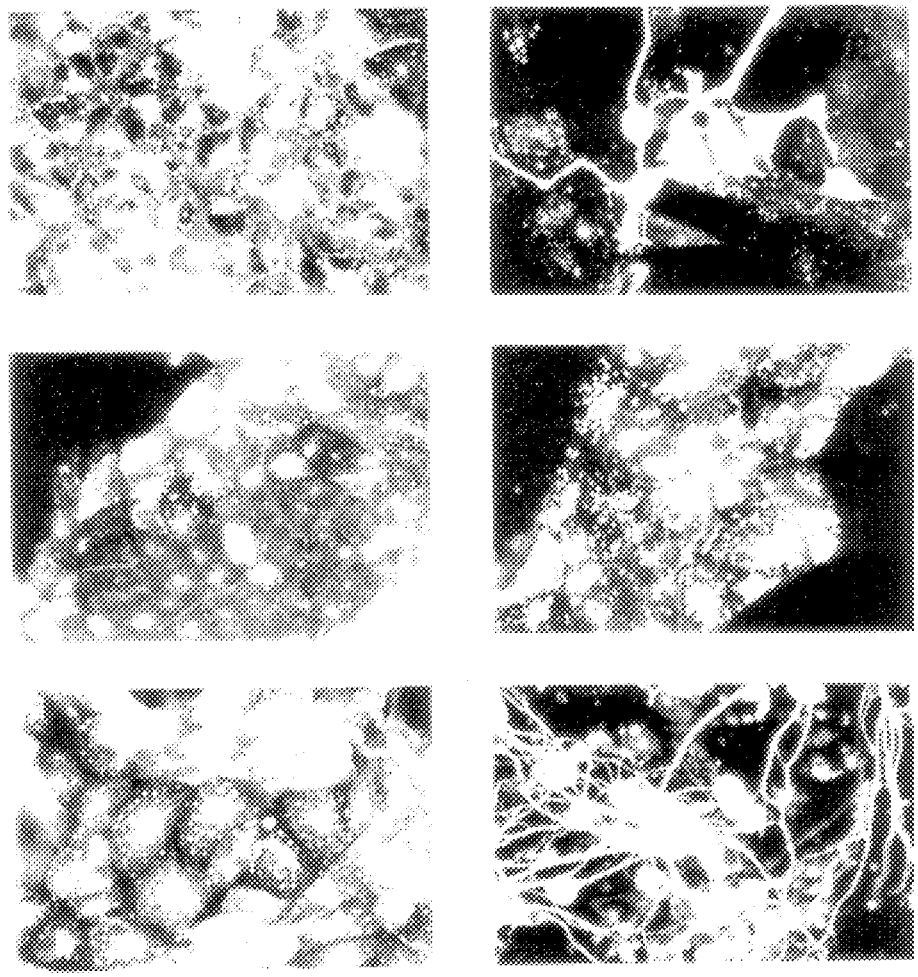
FIG. 3C shows the modulation of neuronal differentiation of P19EC cells by different levels of expression of calreticulin: (D) shows the increased levels of calreticulin inhibit neuronal differentiation. (F) shows the decreased levels of calreticulin enhance neuronal differentiation.

FIG. 3C clearly shows the inhibition of neuronal differentiation by calreticulin overexpression and enhanced differentiation by diminished calreticulin expression.

The effect of calreticulin levels on retinoic acid induced neuronal differentiation occurs via the direct regulation of retinoic acid responsive genes, as demonstrated by an inverse relationship between calreticulin expression level and RARE-driven luciferase gene expression (Dedhar et al., 1994). Furthermore, the endogenous regulation of expression of the retinoic acid responsive genes, CRABPII (Giguere et al., 1990) and RAR-b (de The, et al., 1990; Sucov et al., 1990) are substantially decreased in Cal-1 transfectants, but are either unchanged or slightly increased in the calreticulin-antisense Cal-2 transfectants (Dedhar et al., 1994).

Collectively, these results demonstrate that calreticulin, by binding to the conserved KXFFX$^1$R sequence [SEQ ID NO.:1] in the DNA binding domain of nuclear hormone receptors (Table I), can modulate gene expression and cellular phenotypes, such as cell differentiation. Calreticulin may also behave as a signal modifier by translocating between the nucleus and the cytoplasm, where it has been shown to bind, via an identical sequence motif, to the intracellular domains of the α-subunits of integrin receptors (Rojiani et al., 1991).

EXAMPLE 6

KLGFFKR [SEQ ID NO.:7] Modulates Retinoic Acid Induced Gene Transcription In Vivo In order to test whether a peptide based on the calreticulin-binding KXGFFKR sequence [SEQ ID No: 30 ]

could modulate retinoic acid induced gene transcription in live cells, the p19 cells were transfected with a reporter vector consisting of a retinoic acid response element fused to the luciferase gene. Since these cells contain endogenous retinoic acid receptors RAR and RXR, treatment with retinoic acid results in an induction of the RARE driven luciferase activity (see Table II).

Cell culture conditions: Mouse embryonic carcinoma (P19) cell, grown in 60 mm dishes in 7.5% donor calf serum, 2.5% fetal calf serum alpha MEM (Gibco/BRL) were treated with the peptides [SEQ ID NOS.:7 and 29] KLGFFKR or KLRFGFK for three hours or overnight for 20 hours at 37° C., 5% $CO_2$. With few exceptions, KLXFFKR [SEQ ID NO.:31] is the peptide sequence specific within the binding domain of all steroid receptors. KLRFGFK [SEQ ID NO.:29] is the scrambled peptide of the above sequence. Subsequently each plate was washed four times with serum free alpha MEM to remove excess peptides and replenished with fresh serum containing media. Cells were then transfected by standard calcium phosphate precipitation method (*Current Protocols in Molecular Biology* 9:1) with 1 microgram bRARE in pTKluc, 1.5 microgram pRSV bgal, 3 microgram pKS (carrier) per 60 mm dish. Following a 16 hour incubation at 37° C. 5% $CO_2$, each plate was washed two times with serum free alphaMEM and replenished with serum containing media supplement with $10^7$M retinoic acid (Sigma R2625) and 800 microgram/ml G418 (Gibco 1181-031). Following another 24 hours incubation cells were washed three times with PBS and each 60 mm dish of cells was lysed in 100 microliters of 1% triton X100, 100 mM $KPO_4$ pH7.8, 1 mM DTT. Cell lysates were stored at −70° C. Prior to luciferase/bgal assays, cell debris were spun out on an Eppendorf microfuge (5415C) at 4° C. full speed for 20 minutes.

Luciferase assay: All reagents were equilibrated to room temperature and each sample was assayed independently. Ten microliters of cell lysate was incubated with 50 microliters of luciferase reagent (Promega E1483) in an Eppendorf tube. Thirty seconds later, the sample was immediately counted in a Beckman scintillation counter (LS60001C) for one minute using an open window. Standards in the range of 0.001 nanogram to 1.0 nanogram was used to establish the linearity of the assay.

Beta-gal assay: Assay was done in a microtitre plate (Linbro 76-232-05). Ten microliters of cell lysate were mixed with 90 microliters of bgal reagent in 88 mM phosphate buffer, 11 mM KCl, 1 mM $MgCl_2$, 55 mM 2 ME, 4.4 mM chlorophenol red b-D-galactopyranoside (BMC 884-308). Incubation period varied from 30 minutes to 2 hours at 37° C. Results were read at 570 nm in an ELISA reader (Dynatech MR5000).

The pre-incubation of these cells with the specific KLGFFKR peptide [SEQ ID NO.:7] resulted in a dose-dependent increase in luciferase activity indicating a stimulation of the retinoic acid receptor mediated gene transcription (Table II). The pre-incubation of a control, scrambled peptide had no such effect. The transfection efficiency was controlled by co-transfection of the α-galactiosidase gene and the subsequent measurement of α-galactosidase activity as described above.

These results provide strong evidence that such peptides based on the $KXFFX^1R$ sequence [SEQ ID NO.:1] can be used to modulate hormone responsiveness by influencing the binding of calreticulin to the hormone receptors in live cells. Thus in the experiment described, [SEQ ID NO.:7] the KLGFFKR was able to effectively compete for calreticulin binding with the KGFFRR sequence [SEQ ID NO.:2] in the retinoic acid receptor. This activated the calreticulin-bound receptors resulting in increased transcriptional activity.

TABLE II

| Preincubations | [SEQ ID NO.:] | OVERNIGHT INCUBATIONS Concentrations micromolar | Luciferase × $10^6$ | Beta-gal | Corrected values luc/bgal |
|---|---|---|---|---|---|
| KLGFFKR | [SEQ ID NO.:7] | 10 | 13 | 0.395 | 32.91 |
| KLGFFKR | [SEQ ID NO.:7] | 50 | 20 | 0.443 | 45.15 |
| KLGFFKR | [SEQ ID NO.:7] | 100 | 28 | 0.452 | 61.95 |
| KLRFGFK | [SEQ ID NO.:29] | 10 | 14 | 0.333 | 42.04 |
| KLRFGFK | [SEQ ID NO.:29] | 50 | 16 | 0.387 | 41.34 |
| KLRFGFK | [SEQ ID NO.:29] | 100 | 14 | 0.434 | 32.26 |
| Controls | | | | | |
| no retinoic acid | | 0 | 0.17 | 0.348 | 0.49 |
| $10^{-7}$ retinoic acid | | 0 | 8.3 | 0.323 | 25.7 |

EXAMPLE 7

Peptides Having Differential Specificities for Disrupting Different Hormone Receptor-Calreticulin Interactions To identify such peptides, we utilize gel mobility shift assays (see Example 3) in which known concentrations of purified recombinant androgen receptor, estrogen receptor, retinoic acid receptors (RAR/RXR and RXR/RXR) (Shago et al., 1994) and vitamin D receptor (Xu et al., 1993) are incubated with known concentrations of either recombinant calreticulin, or calreticulin purified by affinity chromatography on a KLGFFKR affinity column [SEQ ID NO.:7] (see Example 3) in the presence of the respective $^{32}$P-labelled DNA response elements and known concentrations of synthetic peptides based on the $KXFFX^1R$ sequence [SEQ ID NO.:1]. In addition to the linear peptides, some peptides are cyclized by adding cysteine residues at either ends. These experiments result in the identification of peptides which have distinct antagonistic specificities for the interaction of different hormone receptors with calreticulin.

In order to derive peptides which might be specific for one receptor over another one, we have undertaken the synthesis of a series of peptides listed in Table III.

TABLE III

PROPOSED PEPTIDES

| Proposed Peptides | [SEQ ID NO.:] | Variants | Exploring Protection | Exploring Hydrophobic Patch |
|---|---|---|---|---|
| RKFFGK | [SEQ ID NO.:32] | Reversed | X | |
| d(CKGFFKR) | | D-amino acid version | X | |
| FGKKRK | [SEQ ID NO.:33] | another scrambled peptide | X | |
| Ac-KGFFKR | [SEQ ID NO.:34] | Acetylated peptide | X | |
| KGLFKR | [SEQ ID NO.:35] | | | X |
| KGFLKR | [SEQ ID NO.:36] | | | X |
| KGYFKR | [SEQ ID NO.:37] | | | X |
| KGFYKR | [SEQ ID NO.:38] | | | X |
| KGPFKR | [SEQ ID NO.:39] | | | X |
| KGFPKR | [SEQ ID NO.:40] | | | X |
| KFGFKR | [SEQ ID NO.:41] | Inversion | | X |
| KGDFKR | [SEQ ID NO.:42] | | | X |
| KGFKDR | [SEQ ID NO.:43] | | | X |

These peptides are being tested in gel mobility shift assays (described in Example 3) using equivalent concentrations of various receptors: retinoic acid receptors (RAR/RXR), vitamin D receptor (VDR), estrogen receptor (ER), androgen receptor (AR) and glucocorticoid receptor (GR), and their respective DNA response elements. These experiments identify specific peptides for use against individual receptors.

Preliminary experiments using the RAR/RXR, RXR/RXR or VDR/RXR receptors indicate that the KLGFFKR peptide [SEQ ID NO.:7] is 10-fold more potent against the VDR/RXR heterodimer compared to RAR/RXR heterodimer, and is 4-fold more potent against the RXR/RXR heterodimer compared to the RAR/RXR receptor.

Our data have also identified the amino acids within this sequence which are crucial for activity as shown in Table IV.

TABLE IV

Relative Ability of Peptides to Reverse Calreticulin Inhibition of Retinoic Acid receptors (RAR/RXR) Binding to DNA Response Element

| Peptide | [SEQ ID NO.:] | % Reversal |
|---|---|---|
| KLGFFKR | [SEQ ID NO.:7] | 100% |
| KLRFGFK (scrambled sequence) | [SEQ ID NO.:30] | 34% |
| GLGFFKR | [SEQ ID NO.:44] | 45% |
| KLDFFKR | [SEQ ID NO.:45] | 73% |
| KLGRFKR | [SEQ ID NO.:46] | 24% |
| KLGFRKR | [SEQ ID NO.:47] | 20% |
| KLGFFGR | [SEQ ID NO.:48] | 65% |
| KLGFFKG | [SEQ ID NO.:49] | 22% |

The most critical amino acids appear to be F, F, and R in the sequence [SEQ ID NO.:7] KLGFFKR. These three amino acids are completely invariant in all steroid and nuclear hormone receptors as well as in integrins.

Thus using the RAR/RXR system in gel mobility shift assays, the two phenylanines, as well as the terminal arginine, were found to be absolutely essential, since substitution of these resulted in the abrogation of the peptide activity (Table IV).

The peptides identified from these gel mobility shift assays are being used in cellular assays described below.

Retinoic acid-receptor specific peptides: These are tested in the P19 retinoic acid induced neuronal differentiation assay described in Example 5.

Vitamin D-receptor specific peptides: These are tested in the MC3T3-E1 osteoblastic cells which can be induced to differentiate into osteoblasts and form a calcified matrix (mineralize) with vitamin D. The ability to mineralize by monitoring $^{45}$Ca incorporation is determined after treatment with peptides.

Estrogen-receptor specific peptides: These are tested for ability to modulate estrogen-responsive breast cancer cell line proliferation. ER positive cells, e.g. MCF7 and T47-D are used.

Androgen-receptor specific peptides: These are tested in prostate carcinoma LnCAP cells which are androgen responsive and express the androgen-receptor.

Glucocorticoid-receptor specific assays: These are tested in dexamethasone treated peripheral blood lymphocytes.

EXAMPLE 8

Regulation of Endogenous Level of Expression of Calreticulin

In murine P19 embryonal carcinoma cells, overexpression of calreticulin inhibits all-trans retinoic acid responsiveness, whereas downregulating calreticulin by antisense cDNA transfection results in an enhancement of retinoic acid response (see Example 5). In order to determine whether such modulation of calreticulin expression results in changes in the responsiveness to other steroid hormones and vitamins, the PRC-CMV based calreticulin vectors CAL-1 (sense cDNA) and CAL-2 (antisense cDNA) are used to stably transfect mouse osteoblastic cells (MC3T3 E1), chicken osteoclast precursors, normal rat mammary epithelial cells (Darcy et al., 1991) and chemically transformed rat mammary adenocarcinoma cells (ATCC CRL1743), as well as estrogen and progesterone responsive human breast carcinoma cells (MCF-7 and T47-D).

Calreticulin expression levels in these cell types are determined at the outset by Western blot analysis. In addition to utilizing these stable expression vectors, we construct inducible calreticulin expression sense- and antisense-cDNA expression vectors driven by strong metal inducible promoters (Filmus et al., 1992). The inducible vectors allow us to turn calreticulin expression on or off at will. In the MC3T3 cells, 1,25 dihydroxyvitamin D3 has a proliferative effect on these cells at subconfluency, but when added to confluent, mineralizing cultures, it enhances the mineralization process. The transfected cells are analyzed for the level of calreticulin expression by Western blot analysis as described by us previously as well as by Northern blot analysis for mRNA levels. The effect of up or down regulation of calreticulin is determined in terms of the above mentioned responses to 1,25 dihydroxyvitamin D3. In addition, the effect on the expression of vitamin D responsive genes, such as c-fos and integrin b3 subunit (Xu et al., 1993) is determined by Northern blot and Western blot analysis. These cells are transfected with a reporter construct consisting of a vitamin D response element (VDRE) driving the luciferase gene. The luciferase activity in mock transfected versus calreticulin sense- and antisense-cDNA transfected cells (stable and inducible) is then be determined as described by us previously (see Example 6).

Similar experiments are carried out in chicken osteoclast precursors whose differentiation into mature osteoclasts is dependent upon vitamin D (Xu et al., 1993).

The effect of modulating calreticulin levels on the glandular differentiation of normal mammary epithelial cells is examined utilizing a cell culture model of differentiation (Darcy, 1991). Since steroid hormones such as estrogen and progesterone play crucial roles in this differentiation process, the effect of calreticulin on this system is determined. Similarly, the effect of modulating calreticulin expression in mammary carcinoma cell response to estrogen, Tamoxifen, progesterone and retinoic acid is determined. Since in cell lines such as MCF-7, estrogen induces proliferation, whereas Tamoxifen and all-trans retinoic acid inhibit proliferation (Pratt et al., 1993), modulating calreticulin levels results in the augmention of one response preferably over another one. Modulation of calreticulin levels is therapeutically significant in the control of breast cancer.

In addition to altering calreticulin levels by cDNA transfection, we determine whether calreticulin expression is modulated by growth factors, cytokines or steroid hormones and vitamins themselves. Although the promoter of the human calreticulin gene has been cloned and characterized (Michelak, 1992), it does not give any specific clues as to its regulation. In addition, it is conceivable that many compounds could regulate calreticulin levels at a post-transcriptional level. Factors which are known to influence the proliferation and differentiation of the above cell types (e.g. IGF-1 and vitamin D for osteoblasts; IL-6 for osteoclasts; EGF, FGF and TGF-b for mammary epithelial cells) are evaluated initially. We have already determined that 1,25 dihydroxyvitamin D3 upregulates calreticulin mRNA levels in the MC3T3 cells. Knowledge about the endogenous regulation of expression of calreticulin allow in vivo manipulation of nuclear hormone receptor-calreticulin interaction.

EXAMPLE 9

Modulation of Hormone Receptor-Calreticulin Interaction by Peptides, Peptide Mimetics and Antibodies We have demonstrated that synthetic peptides based on the sequence $KXFFX^1R$ [SEQ ID NO.:1] can behave as competitive inhibitors of calreticulin-nuclear hormone receptor interaction (see Example 7). This was demonstrated by gel mobility shift assays. When incubated with the nuclear hormone receptor and calreticulin, the peptides can reverse the ability of calreticulin to inhibit receptor-DNA binding in vitro. Since a scrambled peptide was completely ineffective, this assay can distinguish peptide specificity. These data suggest that the interaction of calreticulin with the nuclear hormone receptors can be manipulated with such peptides.

We use the gel mobility shift assay and androgen receptor as well as the retinoic acid receptors (Shago et al., 1994) to determine which amino acids within the $KXFFX^1R$ sequence [SEQ ID NO.:1] are critical for the calreticulin-receptor interaction. This is done by synthesizing peptides with single amino acid substitutions and then testing them for their activity in gel mobility shift assays as described by us previously (see Example 7). Results from these experiments identify the critical amino acids in this sequence motif required for calreticulin-receptor interaction.

The nuclear hormone receptors can be subdivided into two categories, the steroid receptors, which include the androgen receptor, glucocorticoid receptor, mineralocorticoid receptor and estrogen receptor; and the thyroid hormone/retinoic acid receptor group which includes the retinoic acid receptors, thyroid hormone receptor and vitamin D receptor. Unlike the first category, this later category of receptors bind to their DNA response elements as heterodimers with RXR. The above experiments therefore define the sequence motif for a receptor from each of these two categories i.e. androgen receptor and retinoic acid receptors (RAR/RXR; RXR/RXR). Subsequent experiments are then be carried out with other receptors such as estrogen receptor and vitamin D receptor.

The N-domain of calreticulin (Michalak et al, 1992) has been implicated in the interaction with the glucocorticoid receptor. We have prepared GST-fusion proteins in E. coli consisting of either full length human calreticulin, the N-domain, P-domain or the C-domain. Each of these recombinant proteins is tested in gel mobility shift assays (according to the teaching of Example 3) for their effectiveness in inhibiting receptor-DNA interaction. The receptors we use initially will be the androgen receptor and the retinoic acid receptors. P19 EC cells or Vero cells are also transiently transfected with expression vectors containing the N, P or C calreticulin domains, and their effect on hormone induced gene expression determined as described by us previously (see Example 5). Once we have identified the calreticulin domain which interacts with the receptors we use proteolytic fragments of the recombinant proteins (generated by proteolytic cleavage and purification of peptides by HPLC) to further define the minimal peptide(s) necessary for mediating the interaction. If a sufficiently small peptide is found to be active, then synthetic peptides from within that sequence will be evaluated.

EXAMPLE 10

Preparation and testing of delivery systems for peptide-antagonists of calreticulin nuclear hormone receptor interactions After we identify peptides capable of inhibiting calreticulin-receptor interactions in vitro, we test the efficiency of these peptides on cells. To do this, the peptides are incorporated into cationic lipid vesicles (liposomes, such as lipofectin) and incubated with the cell types described in Example 9. To assess internalization of the peptides, some peptides are conjugated with fluorescein isothiocyanate (FITC). After incubation of the liposomes with the cells for different time periods, the cells are examined by immunoflourescence microscopy to assess intracellular accumulation. The biological effects of the peptides are determined by assessing hormonal sensitivity of the target cells, expression of primary response genes by Northern and Western blot analysis, and hormone-induced expression of luciferase reporter constructs containing various response elements, described in Example 6. The target cells and the hormone responsive parameters to be used are described in Example 7.

These experiments determine whether the peptides defined in Example 7 are functional at the cellular level in antagonizing hormone receptor-calreticulin interactions. Once we optimize the peptide delivery systems and achieve the predictable cellular responses, we test these peptide-liposomes in animal model systems such as bone formation in the mouse, and rat mammary gland differentiation. For the former, primary osteoblasts derived from mouse calvariae are injected into the gluteal muscle of recipient mice where these osteoblasts differentiate to form mineralized nodules. The effect of local or systemic administration of peptide-liposomes are then assessed in this model. Similarly the effect of the peptides on normal mammary gland development after injection of normal rat mammary epithelial cells into mammary fat pads (Darcy, 1991) are assessed. If the peptides are found to be effective in influencing these processes then their effect on animal models of osteoporosis, and growth and differentiation of human breast and prostate cancer xenografts in nude mice are determined.

The following examples relate to the manufacture and use of pharmaceuticals to treat particular diseases, including cancer, osteoporosis, and chronic inflammatory disease, using pharmaceuticals comprising a protein for use in modulating hormone responsiveness and a carrier.

EXAMPLE 11

Method of Treating Prostate Cancer

Prostate cancer is the most frequently diagnosed invasive cancer and the second most common cause of cancer death in men in Western societies (Boring, 1993; Coffey, 1993). At present, prostate cancer patients are diagnosed with either locally invasive, or disseminated disease, and the currently available forms of treatment may prolong survival but are essentially only palliative (Scardino, 1992; Koxlowski, 1991; Santer, 1992).

Although primary endocrine ablation leads to an initial response in about 70% of patients with advanced disease, most patients relapse within three years and only about 20% survive for five years (Kozlowski, 1991). This rapid progression of prostate cancer following failure of primary hormone therapy is attributed to androgen-independent tumor growth.

In some androgen-insensitive rat as well as human prostate cancer cell lines, androgen independence is associated with a loss or decrease in androgen receptor (AR) mRNA and protein levels (Quarmby, 1990; Tilley, 1990). However some prostate carcinoma cell lines derived from metastases retain AR expression and androgen sensitivity (e.g. Ln CAP cell line). Furthermore there is evidence that some prostate cancer cells which continue to grow after initiation of anti-androgen therapy retain expression of AR (van der Kwast, 1991; Tilley, 1994). Similarly, AR expression is retained by androgen-independent mouse mammary tumors (Dabre, 1987).

These observations suggest that mechanisms other than the loss of AR expression are involved in the progression to an androgen-independent state. One explanation could be the presence of mutations in the AR gene in a subpopulation of tumor cells which results in aberrant regulation of growth by steroids. Indeed mutations in the AR gene have been detected in prostate cancer cells, although their significance in tumor progression is not yet clear. Another explanation might be alterations in the expression or function of components which regulate AR activity and AR dependent gene expression.

As described in previous Examples, calreticulin, can bind to nuclear hormone receptors by interacting with the KXFFX$^1$R sequence [SEQ ID NO.:1]. The interaction results in a profound inhibition of nuclear hormone receptor DNA binding activity which can be reversed by soluble competing synthetic peptides with the generic sequence KXFFX$^1$R [SEQ ID NO.:1].

The level of expression of calreticulin in prostate androgen-dependent and independent prostate cancer cells could have significant effects on androgen receptor activity. Furthermore, experimental manipulation of calreticulin levels in prostate cancer cells should also result in the modulation of androgen-receptor activity. In addition, the interaction of androgen receptors with calreticulin could be taken advantage of, theoretically, by utilizing calreticulin or calreticulin-derived peptides and peptide-mimetics for the inhibition of androgen receptor dependent prostate cancer cell growth. Such a therapeutic strategy might be particularly useful in recurrent, androgen-independent prostate cancers which retain expression of AR or mutant ARs and which may bind to DNA in the absence of androgen.

Calreticulin expression in the nuclear, cytoplasmic and microsomal fractions from human prostate carcinoma cell-lines PC-3, DU-145, LnCAP, as well as highly invasive variants of PC-3 cells (IPC31-3) (Dedjar. 1994) is determined by Western blot analysis utilizing two different polyclonal anti-calreticulin antibodies as described by us previously (Leung-Hagesteijn, 1994). Expression at the level of mRNA is carried out using a 1.9 Kb calreticulin cDNA. Calreticulin expression in these cells is determined after treatment with androgens (for LnCAP cells which express AR, or for PC-3 cells transfected with AR, see below), retinoic acid, 1,25 dihydroxy vitamin D3, and growth factors such as epidermal growth factor and insulin-like growth factors.

A subset of a large (>125) tissue bank of frozen human prostate cancers (Sunnybrook Health Science Centre were treated with neo adjuvant androgen ablative therapy prior to resection. Each frozen block has been histologically characterized. The bank also contains hormone-resistant prostate cancer specimens and will accrue fresh bond marrow metastases from warm autopsies on patients dying of androgen resistant prostate cancer. These tissues are freely available for the aforementioned analyses. This permits determination of calreticulin expression in untreated, hormonally treated and hormone resistant disease.

Calreticulin expression in cryostat sections is determined by immunohistochemistry using the avidin-biotin complex method described by Hsu et al., 1981 as well as by in situ hybridization using antisense cDNA calreticulin probes as described by Naylor et al., 1990. These procedures are performed in Dr. Malik's laboratory where they are carried out on a routine basis. Simultaneous determination of the androgen-receptor status in these tissues on serial sections are carried out using anti-AR antibodies (Tilley, 1994).

Overexpression, or inhibition of expression of calreticulin is carried out by stable transfection of sense (pRC-CMV-Cal1) or anti-sense (pRC-CMV-Cal2) (Dedhar, 1994) cDNA expression vectors into LnCAP or AR expressing PC-3 cells. AR expressing PC-3 cells are obtained from Dr. Paul Rennie, Vancouver, B.C. We have previously described the utility of these calreticulin expression vectors in manipulating hormone responsiveness (see Example 4). These cells are also transfected with a tetracyclin inducible calreticulin expression vector. This expression plasmid, pUHD10-3-CAL, has been constructed and calreticulin sense or anti-sense mDNA expression is induced via a tetracyclin-operators. Calreticulin expression levels are determined by Western blot analysis as described above. The responsiveness of the transfected cells to androgens, in terms of cell growth, is then determined. Cell growth is determined by counting cell numbers as well as by 3H-thymidine incorporation. Calreticulin overexpression makes the cells non-responsive to androgens, whereas inhibition of calreticulin expression makes the cells more sensitive, as was the case for retinoic acid responsiveness in ECP19 cells (see Example 5). Stable overexpression of calreticulin does not alter intracellular calcium concentrations, and therefore the observed effects on hormone sensitivity are not due to effects on calcium levels.

The calreticulin transfected cells is compared with the parental or mock transfected cells for their abilities to form tumors in nude mice upon subcutaneous inoculation, or orthotopic inoculation into the prostate gland.

The domain of calreticulin which interacts with the KXFFX$^1$R sequence [SEQ ID NO.:1] has been identified as the globular N-domain. This domain contains a putative ATP binding site and recombinant calreticulin can be phosphorylated in vitro on a serine residue within this domain (Leung-Hagesteijn, 1994) We have prepared GST-domain, fusion proteins in *E. Coli* consisting of the full length human calreticulin, the N-domain, P-domain, or the acidic C-domain. Each of these recombinant peptides is tested in gel mobility shift assays for their effectiveness in the inhibition of androgen receptor-DNA interaction (see Example 9). These domains are tested for their effectiveness in inhibiting androgen mediated gene expressing by transiently expressing them in LnCAP or AR-expression PC-3 cells (described previously). Once we have identified the calreticulin domain which interacts with the androgen receptor (although this is likely to be the N-domain, based on previous work, see above), we derive proteolytic fragments from these proteins (by limited proteolytic cleavage using various proteases, and purification of peptides by high pressure liquid chromatography), and utilize these in gel mobility shift assays to further define the minimal peptide sequence required for interaction with the androgen receptor. If a sufficiently small peptide is found to be active, then synthetic peptides from within that sequence are evaluated further.

Peptides capable of inhibiting AR-DNA interactions in vitro are identified. In order to test the efficiency of these peptides in cells, the peptides are incorporated into cationic lipid vesicles (liposomes, such as lipofectin) and incubated with the cell types (see Example 10).

These experiments determine whether the peptides defined above are functional at the cellular level in antagonizing hormone receptor-DNA interactions. Once we have optimized the peptide delivery systems and achieve the predictable cellular responses, we test these peptide-liposomes in animal model systems described above.

These peptides, in conjunction with current protocols of androgen ablation, are useful in inhibiting androgen-receptor mediated prostate cancer cell growth. This strategy is useful not only in the early treatment of androgen-sensitive tumors, but also in more advanced androgen-resistant tumors which may express normal or mutated ARs which can induce cell growth in an androgen-independent manner. In such tumors, the maintenance of high levels of calreticulin expression, or of adminstration of calreticulin-based peptides (derived as described above), or peptide mimetics, provide a new mode of therapeutic intervention in the inhibition of prostate cancer cell growth and progression.

EXAMPLE 12

Method of Treating Breast Cancer

Here, we use a similar protocol as for prostate cancer (Example 11) but use proteins/mimetic selective for estrogen. Transfections are made into MCF-7, T47-D human breast cancer cells lines instead of LnCAP. For patient treatment, the peptides or their mimetics, or calreticulin or its mimetics are delivered in lipid vesicles prepared as described in Examples 10 and 11.

EXAMPLE 13

Method of Treating Chronic Inflammatory Disease

The debilitating symptoms of chronic inflammatory diseases such as arthritis arise from inadvertent immune responses. Steroidal compounds are major immunosuppressive agents often used in the therapy of chronic inflammatory diseases. The response to such therapy may be dramatically augmented by the co-administration of calreticulin-hormone receptor antagonists based on the KXFFX$^1$R [SEQ ID NO.:1] sequence. Such peptides, or their organic mimetics, may dramatically enhance the hormonal response by activating those receptors which may be bound by calreticulin. This may also result in the use of lower concentrations of the steroidal compounds, resulting in fewer side effects. The mode of delivery of such peptides or organic mimetics would be in lipid vesicles described in Examples 10 and 11.

EXAMPLE 14

Method of Treating Osteoporosis

Osteoporosis results from an imbalance in the rate of bone resorption versus bone formation. Specifically, in post menopausal women, the decrease in systemic estrogen levels results in decreased bone formation in the face of continual osteoclast mediated bone resorption. Estrogen therapy, by using estrogen analogs which may specifically enhance osteoblast function and bone formation is under intensive study. The co-administration of KXFFX$^1$R [SEQ ID NO.:1] based peptides or mimetics specific for the antagonism of calreticulin-estrogen receptor interaction would be highly beneficial for this treatment. Such peptides or mimetics may dramatically increase the efficacy of estrogen analogs used in such therapy.

An alternative approach for the use of calreticulin based therapy might be inhibition of osteoclast differentiation. The differentiation of mature osteoclasts from osteoclast precursors is enhanced by Vitamin D3. The specific inhibition of the vitamin D receptor by calreticulin based mimetics could therefore result in the suppression of osteoclast mediated bone resorption. Combined therapy of increasing bone formation and down regulating bone resorption may be an effective treatment for osteoporosis.

The peptides or mimetics would once again be delivered by methods described in Examples 10 and 11.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

CITED DOCUMENTS

The documents listed below are incorporated herein by reference to the extent that they supplement, explain, provide a background for, or teach methodology, techniques and/or compositions employed herein.

Alexander, J. E., Hunt, D. F., Lee, M. K., et al. Proc. Natl. Acad. Sci. U.S.A. 88, 4685–4689 (1991).

Baksh, S. & Michalak, M. *J. Biol. Chem.* 266, 21458–21465 (1991).

Boring, C. C., et al, *CA Cancer J. Clin.* 43:7, 1993.

Burns, K., Duggan, B., Atkinson, E. A., Famulski, K. S., Nemer, M., Bleakley, R. C., and Michalak, M. Modulation of gene expression by calreticulin binding to the glucocorticoid receptor. Nature, 367: 476–480, 1994.

Carson-Jurica, M., Schrader, W. T. & O'Malley, B. W. Endocrine Rev. 11, 201–220 (1990).

Coffey, D. S., *Cancer* 71 (suppl 3):880, 1993.

Dabre, P. D., et al, *Cell* 51:521, 1987.
Darcy, K. M. Exp. Cell Res., 196: 49–65, 1991.
de The, H., Marchio, A., Tiollais, P. & Dejean, A. *Nature* 343, 1771–1780 (1990).
Dedhar, S., et al, Clin. Exp. Metastasis 11:391, 1993.
Dedhar, S., Rennie, P.S., Shago, M., Leung-Hagesteijn, C., Yang, H., Filmus, J., Hawley, R. G., Bruchovsky, N., Cheng, H., Matusik, R. J., and Giguere, V. Inhibition of Nuclear Hormone Receptor Activity by calreticulin. Nature, 367: 480–483, 1994.
Dedhar, S., Robertson, K. & Gray, V. *J. Biol. Chem.* 266, 21846–21852 (1991).
Dedhar, S., *TIBS* 19:269, 1994.
Filmus, J., Remani, J., and Klein, M. H. Synergistic induction of promoters containing metal- and glucocorticoid-responsive elements. Nucleic Acids Res., 20: 2755–2760, 1992.
Fliegel, L., Burns, K., MacLennan, D. H., Reitheimer, R. A. F. & Michalak, M. J. Biol. Chem. 264, 21522–21528 (1989).
Fuller, P. *J. FASEB J.* 5, 3092–3099 (1991).
Giguere, V., Lyn, S., Yin, P. et al., Proc. Natl. Acad. Sci. U.S.A. 87, 6233–6237 (1990).
Hard, T., Kellenbach, E., Bochens, R., et al. Science 249, 157–160 (1990).
Hsu, S. M., et al, *J. Histochem. Cytochem.* 29:577, 1981.
Kozlowski, J. M. & et al., (1991) *The Urologic Clinics of North America*(W. B. Saunders Co., Philadelphia), p. 15–24.
Lebeau, M.-C., Massol, N., Herrick, J. , et al. J. Biol. Chem. 267, 4281–4284 (1992).
Lee, M. K., Tuttle, J. B. & Rebhun, L. I., et al. Cell Motil. Cytoskel. 17, 118–132 (1 990).
Leung-Hagesteijn, C., et al, *J. Cell Sci.* 107:589, 1994.
Luisi, B. F., Xu, W. X., Otwinowski, Z., Freedman, L. P., Yamamoto, K. R., and Sigler, P. B. Crystallographic analysis of the interaction of the glucocorticoid receptor with DNA. Nature, 352: 497–505, 1991.
Marzluff, W. F. & Huang, R. C. C. in Transcription and Translation: A practical approach 89–129 (Oxford University Press, Oxford, 1985).
McBurney, M. W. & Rogers, B. J. *Dev. Biol.* 89, 503 (1982).
McCauliffe, D. P., Lux, F. A., Liu, T. S. , et al. J. Clin. Invest 85,1379–1391 (1990).
McCauliffe, D. P., Zappi, E., Liu, T. S., Michalak, M., Sontheimer, R. D. & Capra, J. D. J. Clin. Invest. 86, 332–335 (1990).
Michalak, M., et al, Biochem. J. 285:681, 1992.
Michalak, M., Milner, R. E., Burns, K., and Opas, M. Calreticulin. Biochem. J., 285: 681, 1992.
Morrison, N. A. Nature, 367: 284–287, 1994.
Naylor, S. M., et al, *Eur. J. Biochem.* 26:1027, 1990.
O'Malley, B. W. The steroid hormone receptor superfamily: more excitement for the future. Mol. Endocrin., 4: 363–369, 1990.
Opas, M., Dziak, E., Fliegel, L., and Michalak, M. Regulation of expression and intracellular distribution of calreticulin, a major calcium binding protein of non-muscle cells. J. Cell. Physiol., 149: 160–171, 1991.
Pratt, S. E. and Pollak, M. *Cancer Res.,* 53: 5193–5198, 1993.
Quarmby, V. E., et al, *Cancer Res.* 50:735, 1990.
Rennie, P. S., Bruchovsky, N., Leco, K. J., et al. *Mol. Endocrin.* 7, 23–36 (1993).
Rojiani, M., Finlay, B. B., Gray, V. & Dedhar, S. Biochemistry 30, 9859–9866 (1991).
Santer, R. J., *J. Clin. Endocrinol. Metab.* 75:685, 1992.
Scardino, P. T., et al, *Human Pathol.* 23:211, 1992.
Schwabe, J. W. R., Chapman, L., Finch, J. T., and Rhodes, D. The crystal struture of the estrogen receptor DNA-binding domain bound to DNA: how receptors discriminate between their response elements. Cell, 75: 567–578, 1993.
Seed, B. & Sheen, J. Y. *Gene* 67, 271 (1988).
Shago, M., Flock, G., Leung-Hagesteijn, C., Giguere, V., and Dedhar, S. Modulation of the retinoic acid and retinoid X receptor signalling pathways in P19 embryonal carcinoma cells by the calcium binding protein calreticulin. *Cell Growth and Differentiation*, Submitted, (year).
Sucov, H., Murakami, K.K. & Evans, R. M. Proc. Natl. Acad. Sci. U.S.A. 87, 5392–5396 (1990).
Tai, P.-K. K., Albers, M. W., Chang, H., Saber, L. E. & Schreiber, S. L. Science 256, 1315–1318 (1992).
Tilley, W. D., et al, *Cancer Res.* 50:5382, 1990.
Tilley, W. D., et al, Cancer Res. 54:4096, 1994.
Tini, M., Otulakowski, G., Breitman, M. L. et al., Genes & Dev. 7, 295–307 (1993).
van der Kwast, T. H., et al, *Int. J. Cancer* 48:189, 1991.
Xu, C., Ross, F. P., Zhang, L., MacDonald, P. N., Chappel, J., and Teitelbaum, S. L. Cloning of the promoter for the avian integrin b3 subunit gene and its regulation by 1,25 dihydroxyvitamin D3. J. Biol. Chem., 268: 27371–27380, 1993.

We claim:

1. An isolated and purified peptide of 6 amino acids having the amino acid sequence KXFFX$^1$R (SEQ ID NO.:1), wherein X is G, A or V and wherein X$^1$ is K or R and wherein the peptide binds calreticulin.

2. A pharmaceutical composition comprising a carrier and a peptide consisting of all or a portion of the N domain of calreticulin which peptide binds the amino acid sequence KXFFX$^1$R (SEQ ID NO.:1), wherein X is G A or V and wherein X$^1$ is K or R.

3. The pharmaceutical composition of claim 2, wherein the carrier is a lipid vesicle.

4. An isolated and purified synthetic peptide of 6 amino acids having the amino acid sequence selected from the group consisting of KGFFRR (aa 6–11 of SEQ ID NO.:18) KVFFKR (SEQ ID NO.:3), KAFFKR (aa 6–11 of SEQ ID NO.:24), KGFFKR (aa 6–11 of SEQ ID NO.:25), TGFFKR (aa 6–11 of SEQ ID NO.:26), RKFFGK (SEQ ID NO.:32), d(CKGFFKR), FGKKRK (SEQ ID NO.:33), Ac-KGFFKR (SEQ ID NO.:34), KGLFKR (SEQ ID NO.:35), KGFLKR (SEQ ID NO.:36), KGYFKR (SEQ ID NO.:37), KGFYKR (SEQ ID NO.:38), KGPFKR (SEQ ID NO.:39), KGFPKR (SEQ ID NO.:40), KFGFKR (SEQ ID NO.:41), KGDFKR (SEQ ID NO.:42).

5. An isolated and purified synthetic peptide comprising the amino acids sequence selected from a group consisting of GLGFFKR (SEQ ID NO.:44), KLDFFKR (SEQ ID NO.:45), and KLGFFGR (SEQ ID NO.:48), wherein the peptide binds calreticulin.

6. A pharmaceutical composition comprising the peptide of claim 1 and a carrier.

7. The pharmaceutical composition of claim 6 wherein the carrier is a lipid vesicle.

8. A pharmaceutical composition comprising the peptide of claim 4 and a carrier.

9. The pharmaceutical composition of claim 8 wherein the carrier is a lipid vesicle.

10. A pharmaceutical composition comprising the peptide of claim 5 and a carrier.

11. The pharmaceutical composition of claim 10 wherein the carrier is a lipid vesicle.

* * * * *